United States Patent
Bloom et al.

(10) Patent No.: US 9,333,027 B2
(45) Date of Patent: May 10, 2016

(54) METHOD OF PRODUCING AN ELECTROSURGICAL DEVICE

(71) Applicant: MEDTRONIC ADVANCED ENERGY LLC, Minneapolis, MN (US)

(72) Inventors: Eliot F. Bloom, Hopkinton, NH (US); Lorenzo C. Vaccarella, Newmarket, NH (US); Chad M. Greenlaw, Somersworth, NH (US); Roger D. Greeley, Portsmouth, NH (US); Steven G. Miller, Milton, NH (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 253 days.

(21) Appl. No.: 14/045,185

(22) Filed: Oct. 3, 2013

(65) Prior Publication Data

US 2014/0026395 A1    Jan. 30, 2014

Related U.S. Application Data

(63) Continuation of application No. 12/790,309, filed on May 28, 2010, now abandoned.

(51) Int. Cl.
  *H05K 3/34*   (2006.01)
  *A61B 18/14*  (2006.01)
  *A61B 18/00*  (2006.01)

(52) U.S. Cl.
  CPC .............. *A61B 18/14* (2013.01); *A61B 18/148* (2013.01); *A61B 18/1482* (2013.01); *A61B 2018/00029* (2013.01); *Y10T 29/49002* (2015.01)

(58) Field of Classification Search
  CPC ............... Y10T 29/49144; H01L 2924/01079
  USPC .......................................................... 29/840
  See application file for complete search history.

(56) References Cited

U.S. PATENT DOCUMENTS

| | | | |
|---|---|---|---|
| 2,888,928 A | | 6/1959 | Seiger |
| 3,682,130 A | * | 8/1972 | Jeffers .......................... 116/218 |
| 3,750,650 A | | 8/1973 | Ruttgers |
| 3,827,436 A | * | 8/1974 | Stumpf et al. .................. 606/23 |
| 3,830,239 A | * | 8/1974 | Stumpf et al. .................. 606/25 |
| 3,859,986 A | * | 1/1975 | Okada et al. .................. 600/104 |
| 3,862,627 A | * | 1/1975 | Hans, Sr. ....................... 600/387 |
| 3,886,945 A | * | 6/1975 | Stumpf et al. .................. 606/26 |
| 3,907,339 A | * | 9/1975 | Stumpf et al. ............. 285/222.1 |
| 3,910,277 A | * | 10/1975 | Zimmer .......................... 606/23 |
| 3,913,581 A | * | 10/1975 | Ritson et al. .................... 606/23 |
| 3,924,628 A | * | 12/1975 | Droegemueller et al. ...... 606/21 |

(Continued)

FOREIGN PATENT DOCUMENTS

WO    2011/088387    7/2011

*Primary Examiner* — Paul D Kim
(74) *Attorney, Agent, or Firm* — Jeffrey J. Hohenshell

(57) ABSTRACT

A method of producing an electrosurgical device is disclosed. Opposing longitudinal clamshells are formed, and each clamshell includes a face having a generally planar major portion. Longitudinal grooves are formed in a clamshell, and an electrical conductor in a disposed in a groove. The faces are aligned to form an electrical passage including the electrical conductor in the groove and a spaced-apart fluid passage with another groove. The clamshells are welded together to form a shaft member such that the electrical passage and the fluid passage are fluid tight along a major longitudinal portion of the shaft. Electrodes are attached to the distal end of the shaft and are in electrical communication with the electrical conductor.

21 Claims, 11 Drawing Sheets

(56) References Cited

U.S. PATENT DOCUMENTS

| | | | | |
|---|---|---|---|---|
| 4,018,227 A | * | 4/1977 | Wallach | 606/23 |
| 4,022,215 A | * | 5/1977 | Benson | 606/23 |
| 4,060,088 A | * | 11/1977 | Morrison et al. | 606/49 |
| 4,061,135 A | * | 12/1977 | Widran et al. | 600/111 |
| 4,063,560 A | * | 12/1977 | Thomas et al. | 606/23 |
| 4,072,152 A | * | 2/1978 | Linehan | 606/23 |
| 4,082,096 A | | 4/1978 | Benson | |
| 4,207,897 A | * | 6/1980 | Lloyd et al. | 606/23 |
| 4,244,371 A | | 1/1981 | Farin | |
| 4,248,224 A | * | 2/1981 | Jones | 604/508 |
| 4,275,734 A | * | 6/1981 | Mitchiner | 606/23 |
| 4,276,874 A | | 7/1981 | Wolvek et al. | |
| 4,278,090 A | * | 7/1981 | van Gerven | 606/23 |
| 4,321,931 A | | 3/1982 | Hon | |
| 4,342,218 A | | 8/1982 | Fox | |
| 4,355,642 A | | 10/1982 | Alferness | |
| 4,377,168 A | * | 3/1983 | Rzasa et al. | 606/24 |
| 4,381,007 A | | 4/1983 | Doss | |
| 4,519,389 A | * | 5/1985 | Gudkin et al. | 606/20 |
| 4,598,698 A | * | 7/1986 | Siegmund | 600/131 |
| 4,601,290 A | * | 7/1986 | Effron et al. | 606/170 |
| 4,664,110 A | * | 5/1987 | Schanzlin | 606/20 |
| 4,671,274 A | | 6/1987 | Scrochenko | |
| 4,736,749 A | * | 4/1988 | Lundback | 600/387 |
| 4,779,611 A | * | 10/1988 | Grooters et al. | 600/116 |
| 4,802,475 A | * | 2/1989 | Weshahy | 606/21 |
| 4,815,470 A | * | 3/1989 | Curtis et al. | 600/459 |
| 4,872,346 A | * | 10/1989 | Kelly-Fry et al. | 73/627 |
| 4,916,922 A | * | 4/1990 | Mullens | 62/384 |
| 4,917,095 A | * | 4/1990 | Fry et al. | 600/459 |
| 4,919,129 A | | 4/1990 | Weber et al. | |
| 4,931,047 A | | 6/1990 | Broadwin et al. | |
| 4,932,952 A | * | 6/1990 | Wojciechowicz, Jr. | 606/49 |
| 4,936,281 A | * | 6/1990 | Stasz | 600/439 |
| 4,943,290 A | * | 7/1990 | Rexroth et al. | 606/45 |
| 4,946,460 A | * | 8/1990 | Merry et al. | 606/24 |
| 4,950,232 A | * | 8/1990 | Ruzicka et al. | 604/43 |
| 4,985,030 A | * | 1/1991 | Melzer et al. | 606/51 |
| 4,998,933 A | * | 3/1991 | Eggers et al. | 606/41 |
| 5,013,312 A | | 5/1991 | Parins et al. | 606/37 |
| 5,029,574 A | * | 7/1991 | Shimamura et al. | 600/116 |
| 5,044,165 A | * | 9/1991 | Linner et al. | 62/55.5 |
| 5,078,713 A | * | 1/1992 | Varney | 606/23 |
| 5,080,102 A | * | 1/1992 | Dory | 600/439 |
| 5,080,660 A | * | 1/1992 | Buelna | 606/45 |
| 5,100,388 A | * | 3/1992 | Behl et al. | 604/113 |
| 5,108,390 A | * | 4/1992 | Potocky et al. | 606/21 |
| 5,147,355 A | * | 9/1992 | Friedman et al. | 606/23 |
| 5,178,133 A | * | 1/1993 | Pena | 600/203 |
| 5,190,541 A | * | 3/1993 | Abele et al. | 606/46 |
| 5,195,959 A | * | 3/1993 | Smith | 604/34 |
| 5,197,964 A | * | 3/1993 | Parins | 606/48 |
| 5,207,674 A | * | 5/1993 | Hamilton | 606/20 |
| 5,217,860 A | * | 6/1993 | Fahy et al. | 435/1.2 |
| 5,222,501 A | * | 6/1993 | Ideker et al. | 600/439 |
| 5,224,943 A | * | 7/1993 | Goddard | 606/20 |
| 5,228,923 A | * | 7/1993 | Hed | 136/208 |
| 5,231,995 A | * | 8/1993 | Desai | 607/123 |
| 5,232,516 A | * | 8/1993 | Hed | 136/204 |
| 5,234,428 A | * | 8/1993 | Kaufman | 606/45 |
| 5,254,116 A | * | 10/1993 | Baust et al. | 606/23 |
| 5,254,117 A | * | 10/1993 | Rigby et al. | 606/46 |
| 5,263,493 A | * | 11/1993 | Avitall | 607/122 |
| 5,269,291 A | * | 12/1993 | Carter | 606/128 |
| 5,275,595 A | * | 1/1994 | Dobak, III | 606/23 |
| 5,277,201 A | * | 1/1994 | Stern | 607/98 |
| 5,281,213 A | * | 1/1994 | Milder et al. | 606/15 |
| 5,281,215 A | * | 1/1994 | Milder | 606/20 |
| 5,295,484 A | * | 3/1994 | Marcus et al. | 600/439 |
| 5,309,896 A | * | 5/1994 | Moll et al. | 600/207 |
| 5,316,000 A | * | 5/1994 | Chapelon et al. | 600/439 |
| 5,317,878 A | * | 6/1994 | Bradshaw et al. | 62/6 |
| 5,318,525 A | * | 6/1994 | West et al. | 604/95.04 |
| 5,322,520 A | * | 6/1994 | Milder | 604/265 |
| 5,323,781 A | | 6/1994 | Ideker et al. | |
| 5,324,255 A | * | 6/1994 | Passafaro et al. | 604/22 |
| 5,324,284 A | * | 6/1994 | Imran | 606/15 |
| 5,324,286 A | * | 6/1994 | Fowle | 606/23 |
| 5,330,521 A | * | 7/1994 | Cohen | 607/122 |
| 5,334,181 A | * | 8/1994 | Rubinsky et al. | 606/22 |
| 5,334,193 A | * | 8/1994 | Nardella | 606/41 |
| 5,336,220 A | * | 8/1994 | Ryan et al. | 604/22 |
| 5,348,554 A | * | 9/1994 | Imran et al. | 606/41 |
| 5,353,783 A | * | 10/1994 | Nakao et al. | 600/106 |
| 5,354,258 A | * | 10/1994 | Dory | 601/3 |
| 5,361,752 A | * | 11/1994 | Moll et al. | 600/205 |
| 5,383,874 A | | 1/1995 | Jackson et al. | 606/1 |
| 5,385,148 A | * | 1/1995 | Lesh et al. | 600/471 |
| 5,395,312 A | * | 3/1995 | Desai | 604/22 |
| 5,396,887 A | * | 3/1995 | Imran | 600/374 |
| 5,397,304 A | * | 3/1995 | Truckai | 604/528 |
| 5,400,770 A | * | 3/1995 | Nakao et al. | 606/116 |
| 5,400,783 A | * | 3/1995 | Pomeranz et al. | 600/374 |
| 5,401,272 A | * | 3/1995 | Perkins | 606/15 |
| 5,403,309 A | * | 4/1995 | Coleman et al. | 606/20 |
| 5,403,311 A | * | 4/1995 | Abele et al. | 606/49 |
| 5,405,376 A | * | 4/1995 | Mulier et al. | 607/127 |
| 5,409,483 A | * | 4/1995 | Campbell et al. | 606/15 |
| 5,417,709 A | * | 5/1995 | Slater | 606/205 |
| 5,423,807 A | * | 6/1995 | Milder | 606/20 |
| 5,423,811 A | | 6/1995 | Imran et al. | |
| 5,427,119 A | * | 6/1995 | Swartz et al. | 600/585 |
| 5,431,168 A | * | 7/1995 | Webster, Jr. | 600/435 |
| 5,431,649 A | * | 7/1995 | Mulier et al. | 606/41 |
| 5,433,708 A | * | 7/1995 | Nichols et al. | 604/113 |
| 5,435,308 A | * | 7/1995 | Gallup et al. | 600/342 |
| 5,437,651 A | * | 8/1995 | Todd et al. | 604/313 |
| 5,441,503 A | * | 8/1995 | Considine et al. | 606/115 |
| 5,443,463 A | * | 8/1995 | Stern et al. | 606/51 |
| 5,443,470 A | * | 8/1995 | Stern et al. | 607/98 |
| 5,445,638 A | * | 8/1995 | Rydell et al. | 606/51 |
| 5,450,843 A | * | 9/1995 | Moll et al. | 600/207 |
| 5,452,582 A | * | 9/1995 | Longsworth | 62/51.2 |
| 5,452,733 A | * | 9/1995 | Sterman et al. | 128/898 |
| 5,460,629 A | * | 10/1995 | Shlain et al. | 606/46 |
| 5,462,545 A | * | 10/1995 | Wang et al. | 606/41 |
| 5,465,717 A | * | 11/1995 | Imran et al. | 600/374 |
| 5,469,853 A | * | 11/1995 | Law et al. | 600/463 |
| 5,472,876 A | | 12/1995 | Fahy | |
| 5,478,309 A | * | 12/1995 | Sweezer et al. | 604/6.14 |
| 5,478,330 A | * | 12/1995 | Imran et al. | 604/526 |
| 5,486,193 A | * | 1/1996 | Bourne et al. | 606/194 |
| 5,487,385 A | * | 1/1996 | Avitall | 600/374 |
| 5,487,757 A | * | 1/1996 | Truckai et al. | 604/264 |
| 5,490,819 A | * | 2/1996 | Nicholas et al. | 600/201 |
| 5,496,312 A | * | 3/1996 | Klicek | 606/34 |
| 5,497,774 A | * | 3/1996 | Swartz et al. | 600/585 |
| 5,498,248 A | | 3/1996 | Milder | |
| 5,500,012 A | * | 3/1996 | Brucker et al. | 607/122 |
| 5,505,730 A | * | 4/1996 | Edwards | 606/41 |
| 5,516,505 A | * | 5/1996 | McDow | 424/45 |
| 5,520,682 A | * | 5/1996 | Baust et al. | 606/24 |
| 5,522,870 A | * | 6/1996 | Ben-Zion | 607/104 |
| 5,536,267 A | * | 7/1996 | Edwards et al. | 606/41 |
| 5,540,562 A | * | 7/1996 | Giter | 417/254 |
| 5,542,945 A | * | 8/1996 | Fritzsch | 606/48 |
| 5,545,195 A | * | 8/1996 | Lennox et al. | 607/105 |
| 5,545,200 A | * | 8/1996 | West et al. | 607/122 |
| 5,549,661 A | * | 8/1996 | Kordis et al. | 607/99 |
| 5,555,883 A | * | 9/1996 | Avitall | 600/374 |
| 5,556,397 A | * | 9/1996 | Long et al. | 606/48 |
| 5,558,671 A | * | 9/1996 | Yates | 606/38 |
| 5,560,362 A | * | 10/1996 | Sliwa et al. | 600/439 |
| 5,562,702 A | * | 10/1996 | Huitema et al. | 606/207 |
| 5,569,241 A | | 10/1996 | Edwards | |
| 5,569,243 A | * | 10/1996 | Kortenbach et al. | 606/46 |
| 5,571,088 A | * | 11/1996 | Lennox et al. | 604/96.01 |
| 5,571,215 A | * | 11/1996 | Sterman et al. | 600/101 |
| 5,573,532 A | | 11/1996 | Chang et al. | |
| 5,575,766 A | * | 11/1996 | Swartz et al. | 604/508 |
| 5,575,788 A | * | 11/1996 | Baker et al. | 606/41 |
| 5,575,810 A | * | 11/1996 | Swanson et al. | 607/99 |
| 5,578,007 A | | 11/1996 | Imran | |
| 5,582,609 A | * | 12/1996 | Swanson et al. | 606/39 |

(56) References Cited

U.S. PATENT DOCUMENTS

| | | | | |
|---|---|---|---|---|
| 5,588,432 A * | 12/1996 | Crowley | 600/439 |
| 5,590,657 A * | 1/1997 | Cain et al. | 600/439 |
| 5,595,183 A * | 1/1997 | Swanson et al. | 600/510 |
| 5,599,346 A * | 2/1997 | Edwards et al. | 606/41 |
| 5,605,539 A * | 2/1997 | Buelna et al. | 604/508 |
| 5,607,462 A * | 3/1997 | Imran | 607/122 |
| 5,617,854 A * | 4/1997 | Munsif | 600/374 |
| 5,630,837 A * | 5/1997 | Crowley | 601/2 |
| 5,637,090 A * | 6/1997 | McGee et al. | 600/374 |
| 5,643,197 A * | 7/1997 | Brucker et al. | 604/20 |
| 5,647,869 A * | 7/1997 | Goble et al. | 606/37 |
| 5,656,029 A | 8/1997 | Imran et al. | |
| 5,658,278 A | 8/1997 | Imran et al. | |
| 5,671,747 A * | 9/1997 | Connor | 600/459 |
| 5,673,695 A * | 10/1997 | McGee et al. | 600/374 |
| 5,676,662 A * | 10/1997 | Fleischhacker et al. | 606/41 |
| 5,676,692 A * | 10/1997 | Sanghvi et al. | 606/41 |
| 5,676,693 A * | 10/1997 | LaFontaine | 607/116 |
| 5,678,550 A * | 10/1997 | Bassen et al. | 600/431 |
| 5,680,860 A * | 10/1997 | Imran | 600/374 |
| 5,681,278 A * | 10/1997 | Igo et al. | 604/507 |
| 5,681,294 A * | 10/1997 | Osborne et al. | 604/251 |
| 5,681,308 A * | 10/1997 | Edwards et al. | 606/41 |
| 5,687,723 A | 11/1997 | Avitall | |
| 5,687,737 A * | 11/1997 | Branham et al. | 600/523 |
| 5,688,267 A * | 11/1997 | Panescu et al. | 606/41 |
| 5,690,611 A * | 11/1997 | Swartz et al. | 604/528 |
| 5,697,536 A * | 12/1997 | Eggers et al. | 604/114 |
| 5,697,882 A * | 12/1997 | Eggers et al. | 604/114 |
| 5,697,925 A * | 12/1997 | Taylor | 606/34 |
| 5,697,927 A | 12/1997 | Imran et al. | |
| 5,697,928 A * | 12/1997 | Walcott et al. | 606/41 |
| 5,713,942 A | 2/1998 | Stern | |
| 5,716,389 A * | 2/1998 | Walinsky et al. | 607/122 |
| 5,718,241 A * | 2/1998 | Ben-Haim et al. | 600/515 |
| 5,718,701 A * | 2/1998 | Shai et al. | 606/41 |
| 5,720,775 A * | 2/1998 | Larnard | 607/122 |
| 5,722,402 A * | 3/1998 | Swanson et al. | 600/374 |
| 5,730,074 A * | 3/1998 | Peter | 111/118 |
| 5,730,127 A * | 3/1998 | Avitall | 600/374 |
| 5,730,704 A | 3/1998 | Avitall | |
| 5,733,280 A * | 3/1998 | Avitall | 606/23 |
| 5,735,280 A * | 4/1998 | Sherman et al. | 600/1 |
| 5,735,290 A * | 4/1998 | Sterman et al. | 128/898 |
| 5,743,903 A * | 4/1998 | Stern et al. | 606/31 |
| 5,755,760 A * | 5/1998 | Maguire et al. | 607/122 |
| 5,766,167 A * | 6/1998 | Eggers et al. | 606/46 |
| 5,769,846 A | 6/1998 | Edwards et al. | |
| 5,782,828 A * | 7/1998 | Chen et al. | 606/42 |
| 5,785,706 A * | 7/1998 | Bednarek | 606/41 |
| 5,788,636 A * | 8/1998 | Curley | 600/439 |
| 5,792,140 A * | 8/1998 | Tu et al. | 606/41 |
| 5,797,905 A * | 8/1998 | Fleischman et al. | 606/41 |
| 5,797,960 A * | 8/1998 | Stevens et al. | 606/213 |
| 5,800,428 A * | 9/1998 | Nelson et al. | 606/41 |
| 5,800,482 A * | 9/1998 | Pomeranz et al. | 607/101 |
| 5,810,764 A * | 9/1998 | Eggers et al. | 604/23 |
| 5,810,802 A | 9/1998 | Panescu et al. | |
| 5,827,216 A * | 10/1998 | Igo et al. | 604/21 |
| 5,836,947 A * | 11/1998 | Fleischman et al. | 606/47 |
| 5,840,030 A * | 11/1998 | Ferek-Petric et al. | 600/439 |
| 5,843,021 A * | 12/1998 | Edwards et al. | 604/22 |
| 5,843,152 A * | 12/1998 | Tu et al. | 607/122 |
| 5,844,349 A * | 12/1998 | Oakley et al. | 310/358 |
| 5,846,187 A | 12/1998 | Wells et al. | |
| 5,846,191 A * | 12/1998 | Wells et al. | 600/201 |
| 5,849,028 A * | 12/1998 | Chen | 607/102 |
| 5,861,021 A * | 1/1999 | Thome et al. | 607/101 |
| 5,871,523 A | 2/1999 | Fleischman et al. | |
| 5,871,525 A * | 2/1999 | Edwards et al. | 607/104 |
| 5,873,845 A * | 2/1999 | Cline et al. | 601/3 |
| 5,873,855 A | 2/1999 | Eggers et al. | |
| 5,876,399 A * | 3/1999 | Chia et al. | 606/41 |
| 5,879,295 A * | 3/1999 | Li et al. | 600/373 |
| 5,879,296 A * | 3/1999 | Ockuly et al. | 600/374 |
| 5,879,348 A * | 3/1999 | Owens et al. | 606/41 |
| 5,881,732 A * | 3/1999 | Sung et al. | 128/898 |
| 5,882,346 A * | 3/1999 | Pomeranz et al. | 604/525 |
| 5,885,278 A * | 3/1999 | Fleischman | 606/41 |
| 5,891,142 A * | 4/1999 | Eggers et al. | 606/51 |
| 5,893,848 A * | 4/1999 | Negus et al. | 606/41 |
| 5,895,355 A * | 4/1999 | Schaer | 600/381 |
| 5,895,417 A * | 4/1999 | Pomeranz et al. | 607/101 |
| 5,897,553 A * | 4/1999 | Mulier et al. | 606/41 |
| 5,897,554 A * | 4/1999 | Chia et al. | 606/41 |
| 5,899,898 A | 5/1999 | Arless et al. | |
| 5,899,899 A * | 5/1999 | Arless et al. | 606/22 |
| 5,902,289 A | 5/1999 | Swartz et al. | |
| 5,904,711 A * | 5/1999 | Flom et al. | 607/129 |
| 5,906,580 A * | 5/1999 | Kline-Schoder et al. | 600/459 |
| 5,906,587 A * | 5/1999 | Zimmon | 604/514 |
| 5,906,606 A * | 5/1999 | Chee et al. | 604/527 |
| 5,908,029 A * | 6/1999 | Knudson et al. | 128/898 |
| 5,913,854 A * | 6/1999 | Maguire et al. | 606/41 |
| 5,916,213 A * | 6/1999 | Haissaguerre et al. | 606/41 |
| 5,916,214 A * | 6/1999 | Cosio et al. | 606/41 |
| 5,921,924 A * | 7/1999 | Avitall | 600/374 |
| 5,921,982 A * | 7/1999 | Lesh et al. | 606/41 |
| 5,925,045 A * | 7/1999 | Reimels et al. | 606/48 |
| 5,927,284 A * | 7/1999 | Borst et al. | 128/898 |
| 5,928,191 A * | 7/1999 | Houser et al. | 604/95.04 |
| 5,931,810 A * | 8/1999 | Grabek | 604/506 |
| 5,931,848 A * | 8/1999 | Saadat | 606/167 |
| 5,935,123 A | 8/1999 | Edwards et al. | |
| 5,944,715 A * | 8/1999 | Goble et al. | 606/41 |
| 5,954,661 A * | 9/1999 | Greenspon et al. | 600/510 |
| 5,957,919 A | 9/1999 | Laufer | |
| 5,971,980 A * | 10/1999 | Sherman | 606/34 |
| 5,971,983 A | 10/1999 | Lesh | |
| 5,975,919 A * | 11/1999 | Arnett et al. | 439/82 |
| 5,980,516 A * | 11/1999 | Mulier et al. | 606/41 |
| 5,989,248 A * | 11/1999 | Tu et al. | 606/41 |
| 5,993,412 A * | 11/1999 | Deily et al. | 604/68 |
| 5,993,447 A * | 11/1999 | Blewett et al. | 606/50 |
| 6,004,316 A * | 12/1999 | Laufer | 606/28 |
| 6,004,319 A * | 12/1999 | Goble et al. | 606/48 |
| 6,007,499 A * | 12/1999 | Martin et al. | 601/3 |
| 6,010,500 A * | 1/2000 | Sherman et al. | 606/41 |
| 6,012,457 A | 1/2000 | Lesh | |
| 6,015,391 A * | 1/2000 | Rishton et al. | 600/567 |
| 6,016,811 A * | 1/2000 | Knopp et al. | 128/898 |
| 6,018,676 A * | 1/2000 | Davis et al. | 600/431 |
| 6,019,757 A * | 2/2000 | Scheldrup | 606/49 |
| 6,024,733 A * | 2/2000 | Eggers et al. | 604/500 |
| 6,030,381 A * | 2/2000 | Jones et al. | 606/41 |
| 6,036,687 A * | 3/2000 | Laufer et al. | 606/27 |
| 6,042,556 A * | 3/2000 | Beach et al. | 601/3 |
| 6,048,333 A * | 4/2000 | Lennox et al. | 604/113 |
| 6,056,744 A * | 5/2000 | Edwards | 606/41 |
| 6,056,745 A * | 5/2000 | Panescu et al. | 606/42 |
| 6,056,746 A | 5/2000 | Goble | |
| 6,056,747 A * | 5/2000 | Saadat et al. | 606/50 |
| 6,063,081 A * | 5/2000 | Mulier et al. | 606/45 |
| 6,066,139 A * | 5/2000 | Ryan et al. | 606/50 |
| 6,068,653 A * | 5/2000 | LaFontaine | 607/116 |
| 6,071,279 A * | 6/2000 | Whayne et al. | 606/41 |
| 6,083,237 A * | 7/2000 | Huitema et al. | 606/180 |
| 6,086,585 A * | 7/2000 | Hovda et al. | 606/45 |
| 6,088,894 A | 7/2000 | Oakley | |
| 6,096,037 A * | 8/2000 | Mulier et al. | 606/49 |
| 6,113,592 A * | 9/2000 | Taylor | 606/34 |
| 6,113,596 A * | 9/2000 | Hooven et al. | 606/42 |
| 6,117,101 A * | 9/2000 | Diederich et al. | 604/22 |
| 6,120,496 A * | 9/2000 | Whayne et al. | 606/1 |
| 6,141,576 A * | 10/2000 | Littmann et al. | 600/381 |
| 6,142,993 A * | 11/2000 | Whayne et al. | 606/41 |
| 6,142,994 A * | 11/2000 | Swanson et al. | 606/41 |
| 6,149,620 A * | 11/2000 | Baker et al. | 604/22 |
| 6,152,920 A * | 11/2000 | Thompson et al. | 606/41 |
| 6,161,543 A * | 12/2000 | Cox et al. | 128/898 |
| 6,165,174 A * | 12/2000 | Jacobs et al. | 606/41 |
| 6,190,384 B1 * | 2/2001 | Ouchi | 606/47 |
| 6,193,716 B1 * | 2/2001 | Shannon, Jr. | 606/45 |
| 6,210,406 B1 * | 4/2001 | Webster | 606/41 |

(56) References Cited

U.S. PATENT DOCUMENTS

| | | | | |
|---|---|---|---|---|
| 6,210,410 | B1* | 4/2001 | Farin et al. | 606/49 |
| 6,210,411 | B1* | 4/2001 | Hofmann et al. | 606/52 |
| 6,212,426 | B1* | 4/2001 | Swanson | 600/510 |
| 6,217,528 | B1* | 4/2001 | Koblish et al. | 600/585 |
| 6,217,575 | B1* | 4/2001 | DeVore et al. | 606/41 |
| 6,217,576 | B1* | 4/2001 | Tu et al. | 606/41 |
| 6,224,592 | B1 | 5/2001 | Eggers et al. | |
| 6,231,518 | B1* | 5/2001 | Grabek et al. | 600/508 |
| 6,231,591 | B1* | 5/2001 | Desai | 606/210 |
| 6,235,020 | B1* | 5/2001 | Cheng et al. | 606/34 |
| 6,235,024 | B1* | 5/2001 | Tu | 606/41 |
| 6,237,605 | B1* | 5/2001 | Vaska et al. | 128/898 |
| 6,238,347 | B1* | 5/2001 | Nix et al. | 600/463 |
| 6,238,387 | B1* | 5/2001 | Miller, III | 606/34 |
| 6,238,393 | B1* | 5/2001 | Mulier et al. | 606/41 |
| 6,245,061 | B1* | 6/2001 | Panescu et al. | 606/27 |
| 6,245,064 | B1* | 6/2001 | Lesh et al. | 606/34 |
| 6,245,065 | B1* | 6/2001 | Panescu et al. | 606/40 |
| 6,251,092 | B1* | 6/2001 | Qin et al. | 604/95.01 |
| 6,251,110 | B1* | 6/2001 | Wampler | 606/49 |
| 6,251,128 | B1* | 6/2001 | Knopp et al. | 607/100 |
| 6,258,087 | B1* | 7/2001 | Edwards et al. | 606/41 |
| 6,264,650 | B1* | 7/2001 | Hovda et al. | 606/32 |
| 6,266,551 | B1* | 7/2001 | Osadchy et al. | 600/424 |
| 6,270,471 | B1* | 8/2001 | Hechel et al. | 604/22 |
| 6,283,988 | B1* | 9/2001 | Laufer et al. | 607/96 |
| 6,283,989 | B1* | 9/2001 | Laufer et al. | 607/96 |
| 6,293,943 | B1* | 9/2001 | Panescu et al. | 606/41 |
| 6,296,619 | B1* | 10/2001 | Brisken et al. | 604/22 |
| 6,299,633 | B1* | 10/2001 | Laufer | 607/96 |
| 6,302,880 | B1* | 10/2001 | Schaer | 606/41 |
| 6,311,692 | B1* | 11/2001 | Vaska et al. | 128/898 |
| 6,312,383 | B1* | 11/2001 | Lizzi et al. | 600/437 |
| 6,314,962 | B1 | 11/2001 | Vaska et al. | |
| 6,314,963 | B1 | 11/2001 | Vaska et al. | |
| 6,322,559 | B1* | 11/2001 | Daulton et al. | 606/41 |
| 6,325,797 | B1* | 12/2001 | Stewart et al. | 606/41 |
| 6,328,735 | B1* | 12/2001 | Curley et al. | 606/41 |
| 6,328,736 | B1 | 12/2001 | Mulier | |
| 6,332,881 | B1* | 12/2001 | Carner et al. | 606/41 |
| 6,352,533 | B1* | 3/2002 | Ellman et al. | 606/41 |
| 6,358,248 | B1 | 3/2002 | Mulier | |
| 6,361,531 | B1* | 3/2002 | Hissong | 606/27 |
| 6,364,876 | B1* | 4/2002 | Erb et al. | 606/33 |
| 6,368,275 | B1* | 4/2002 | Sliwa et al. | 600/437 |
| 6,371,955 | B1* | 4/2002 | Fuimaono et al. | 606/41 |
| 6,371,956 | B1* | 4/2002 | Wilson et al. | 606/49 |
| 6,383,151 | B1 | 5/2002 | Diederich et al. | |
| 6,385,472 | B1* | 5/2002 | Hall et al. | 600/374 |
| 6,398,792 | B1* | 6/2002 | O'Connor | 606/128 |
| 6,409,722 | B1* | 6/2002 | Hoey et al. | 606/34 |
| 6,413,254 | B1* | 7/2002 | Hissong et al. | 606/27 |
| 6,416,509 | B1* | 7/2002 | Goble et al. | 606/37 |
| 6,419,648 | B1* | 7/2002 | Vitek et al. | 601/3 |
| 6,425,867 | B1* | 7/2002 | Vaezy et al. | 600/439 |
| 6,430,426 | B2 | 8/2002 | Avitall | |
| 6,440,130 | B1 | 8/2002 | Mulier | |
| 6,443,952 | B1 | 9/2002 | Mulier | |
| 6,447,507 | B1* | 9/2002 | Bednarek et al. | 606/41 |
| 6,461,314 | B1* | 10/2002 | Pant et al. | 601/2 |
| 6,461,956 | B1* | 10/2002 | Hsuan et al. | 438/622 |
| 6,464,700 | B1* | 10/2002 | Koblish et al. | 606/41 |
| 6,471,697 | B1 | 10/2002 | Lesh | |
| 6,471,698 | B1 | 10/2002 | Edwards et al. | |
| 6,474,340 | B1 | 11/2002 | Vaska et al. | |
| 6,475,216 | B2 | 11/2002 | Mulier | |
| 6,477,396 | B1* | 11/2002 | Mest et al. | 600/374 |
| 6,478,793 | B1* | 11/2002 | Cosman et al. | 606/34 |
| 6,484,727 | B1 | 11/2002 | Vaska et al. | |
| 6,488,680 | B1* | 12/2002 | Francischelli et al. | 606/41 |
| 6,502,575 | B1 | 1/2003 | Jacobs et al. | |
| 6,508,815 | B1* | 1/2003 | Strul et al. | 606/34 |
| 6,514,250 | B1* | 2/2003 | Jahns et al. | 606/41 |
| 6,517,536 | B2* | 2/2003 | Hooven et al. | 606/41 |
| 6,527,767 | B2* | 3/2003 | Wang et al. | 606/32 |
| 6,537,248 | B2* | 3/2003 | Mulier et al. | 604/114 |
| 6,537,272 | B2* | 3/2003 | Christopherson et al. | 606/34 |
| 6,558,382 | B2* | 5/2003 | Jahns et al. | 606/41 |
| 6,558,385 | B1* | 5/2003 | McClurken et al. | 606/50 |
| 6,575,969 | B1* | 6/2003 | Rittman et al. | 606/41 |
| 6,579,288 | B1* | 6/2003 | Swanson et al. | 606/41 |
| 6,584,360 | B2* | 6/2003 | Francischelli et al. | 607/98 |
| 6,585,732 | B2 | 7/2003 | Mulier | |
| 6,602,248 | B1* | 8/2003 | Sharps et al. | 606/32 |
| 6,603,988 | B2* | 8/2003 | Dowlatshahi | 600/407 |
| 6,605,084 | B2* | 8/2003 | Acker et al. | 606/28 |
| 6,610,055 | B1* | 8/2003 | Swanson et al. | 606/41 |
| 6,610,060 | B2 | 8/2003 | Mulier | |
| 6,613,048 | B2 | 9/2003 | Mulier | |
| 6,635,034 | B1* | 10/2003 | Cosmescu | 604/289 |
| 6,645,199 | B1* | 11/2003 | Jenkins et al. | 606/41 |
| 6,645,202 | B1* | 11/2003 | Pless et al. | 606/41 |
| 6,648,883 | B2* | 11/2003 | Francischelli et al. | 606/41 |
| 6,656,175 | B2* | 12/2003 | Francischelli et al. | 606/41 |
| 6,663,627 | B2* | 12/2003 | Francischelli et al. | 606/41 |
| 6,666,862 | B2* | 12/2003 | Jain et al. | 606/41 |
| 6,679,882 | B1* | 1/2004 | Kornerup | 606/51 |
| 6,682,501 | B1* | 1/2004 | Nelson et al. | 604/22 |
| 6,689,131 | B2* | 2/2004 | McClurken | 606/48 |
| 6,692,450 | B1 | 2/2004 | Coleman | |
| 6,699,240 | B2* | 3/2004 | Francischelli | 606/32 |
| 6,702,810 | B2* | 3/2004 | McClurken et al. | 606/34 |
| 6,702,811 | B2* | 3/2004 | Stewart et al. | 606/41 |
| 6,706,038 | B2 | 3/2004 | Francischelli | |
| 6,706,039 | B2* | 3/2004 | Mulier et al. | 606/41 |
| 6,716,211 | B2 | 4/2004 | Mulier | |
| 6,736,810 | B2 | 5/2004 | Hoey | |
| 6,755,827 | B2 | 6/2004 | Mulier | |
| 6,764,487 | B2 | 7/2004 | Mulier | |
| 6,766,202 | B2* | 7/2004 | Underwood et al. | 607/99 |
| 6,766,817 | B2* | 7/2004 | da Silva | 137/1 |
| 6,773,433 | B2 | 8/2004 | Stewart et al. | |
| 6,775,575 | B2* | 8/2004 | Bommannan et al. | 607/101 |
| 6,776,780 | B2 | 8/2004 | Mulier | |
| 6,807,968 | B2* | 10/2004 | Francischelli et al. | 128/898 |
| 6,827,713 | B2* | 12/2004 | Bek et al. | 606/1 |
| 6,827,715 | B2* | 12/2004 | Francischelli et al. | 606/34 |
| 6,832,996 | B2* | 12/2004 | Woloszko et al. | 606/41 |
| 6,849,073 | B2 | 2/2005 | Hoey | |
| 6,858,028 | B2 | 2/2005 | Mulier | |
| 6,887,238 | B2 | 5/2005 | Jahns | |
| 6,899,711 | B2 | 5/2005 | Stewart et al. | |
| 6,911,019 | B2 | 6/2005 | Mulier | |
| 6,915,806 | B2* | 7/2005 | Pacek et al. | 128/898 |
| 6,916,318 | B2 | 7/2005 | Francischelli | |
| 6,918,404 | B2 | 7/2005 | Dias da Silva | |
| 6,936,046 | B2 | 8/2005 | Hissong | |
| 6,942,661 | B2* | 9/2005 | Swanson | 606/41 |
| 6,949,097 | B2 | 9/2005 | Stewart et al. | |
| 6,949,098 | B2 | 9/2005 | Mulier | |
| 6,953,461 | B2* | 10/2005 | McClurken et al. | 606/51 |
| 6,960,205 | B2 | 11/2005 | Jahns | |
| 6,962,589 | B2 | 11/2005 | Mulier | |
| 7,066,586 | B2 | 6/2006 | da Silva | |
| 7,115,139 | B2 | 10/2006 | McClurken et al. | |
| 7,156,845 | B2 | 1/2007 | Mulier et al. | |
| 7,166,106 | B2* | 1/2007 | Bartel et al. | 606/51 |
| 7,207,471 | B2* | 4/2007 | Heinrich et al. | 227/181.1 |
| 7,232,440 | B2* | 6/2007 | Dumbauld et al. | 606/51 |
| 7,247,155 | B2 | 7/2007 | Hoey et al. | |
| 7,261,711 | B2 | 8/2007 | Mulier et al. | |
| 7,309,325 | B2 | 12/2007 | Mulier et al. | |
| 7,311,708 | B2* | 12/2007 | McClurken | 606/50 |
| 7,322,974 | B2* | 1/2008 | Swoyer et al. | 606/41 |
| 7,361,175 | B2* | 4/2008 | Suslov | 606/49 |
| 7,364,579 | B2 | 4/2008 | Mulier et al. | |
| 7,537,595 | B2 | 5/2009 | McClurken | |
| 7,604,635 | B2 | 10/2009 | McClurken et al. | |
| 7,645,277 | B2 | 1/2010 | McClurken et al. | |
| 7,651,494 | B2 | 1/2010 | McClurken et al. | |
| 7,736,361 | B2* | 6/2010 | Palanker et al. | 606/45 |
| 7,815,634 | B2 | 10/2010 | McClurken et al. | |
| 7,909,820 | B2* | 3/2011 | Lipson et al. | 606/34 |
| 7,976,544 | B2 | 7/2011 | McClurken | |

(56) References Cited

U.S. PATENT DOCUMENTS

| | | |
|---|---|---|
| 7,998,140 B2 | 8/2011 | McClurken |
| 8,012,154 B2 * | 9/2011 | Livneh ............................ 606/52 |
| 8,038,670 B2 | 10/2011 | McClurken |
| 8,083,736 B2 | 12/2011 | McClurken et al. |
| 8,177,783 B2 * | 5/2012 | Davison et al. ................. 606/37 |
| 8,216,233 B2 * | 7/2012 | McClurken et al. ............ 606/48 |
| 8,323,276 B2 * | 12/2012 | Palanker et al. ................ 606/34 |
| 8,348,946 B2 | 1/2013 | McClurken |
| 8,361,068 B2 | 1/2013 | McClurken |
| 2002/0049483 A1 * | 4/2002 | Knowlton .................... 607/101 |
| 2003/0014050 A1 * | 1/2003 | Sharkey et al. ................. 606/45 |
| 2003/0032954 A1 * | 2/2003 | Carranza et al. ............... 606/41 |
| 2003/0045872 A1 | 3/2003 | Jacobs |
| 2003/0073993 A1 * | 4/2003 | Ciarrocca ....................... 606/41 |
| 2003/0144656 A1 * | 7/2003 | Ocel et al. ....................... 606/41 |
| 2003/0191462 A1 | 10/2003 | Jacobs |
| 2003/0204185 A1 * | 10/2003 | Sherman et al. ................ 606/41 |
| 2003/0216724 A1 * | 11/2003 | Jahns ............................. 606/41 |
| 2004/0015106 A1 * | 1/2004 | Coleman ........................... 601/3 |
| 2004/0015219 A1 * | 1/2004 | Francischelli ................ 607/104 |
| 2004/0024395 A1 * | 2/2004 | Ellman et al. .................. 606/37 |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 * | 4/2004 | Stewart et al. .................. 606/41 |
| 2004/0087940 A1 * | 5/2004 | Jahns et al. ..................... 606/41 |
| 2004/0092926 A1 | 5/2004 | Hoey |
| 2004/0111136 A1 | 6/2004 | Sharkey et al. |
| 2004/0111137 A1 * | 6/2004 | Shankey et al. .............. 607/101 |
| 2004/0116923 A1 * | 6/2004 | Desinger ........................ 606/50 |
| 2004/0138621 A1 * | 7/2004 | Jahns et al. ................... 604/173 |
| 2004/0138656 A1 | 7/2004 | Francischelli |
| 2004/0143260 A1 | 7/2004 | Francischelli |
| 2004/0186465 A1 * | 9/2004 | Francischelli et al. .......... 606/34 |
| 2004/0215183 A1 | 10/2004 | Hoey |
| 2004/0220560 A1 * | 11/2004 | Briscoe .......................... 606/32 |
| 2004/0236322 A1 | 11/2004 | Mulier |
| 2004/0267326 A1 | 12/2004 | Ocel |
| 2005/0010095 A1 * | 1/2005 | Stewart et al. ................ 600/374 |
| 2005/0033280 A1 | 2/2005 | Francischelli |
| 2005/0090815 A1 * | 4/2005 | Francischelli et al. .......... 606/32 |
| 2005/0143729 A1 | 6/2005 | Francischelli |
| 2005/0165392 A1 | 7/2005 | Francischelli |
| 2005/0209564 A1 * | 9/2005 | Bonner et al. ................. 604/173 |
| 2005/0267454 A1 * | 12/2005 | Hissong et al. ................. 606/27 |
| 2006/0009756 A1 * | 1/2006 | Francischelli et al. .......... 606/32 |
| 2006/0009759 A1 * | 1/2006 | Chrisitian et al. .............. 606/41 |
| 2006/0064085 A1 * | 3/2006 | Schechter et al. .............. 606/50 |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0021450 A1 | 1/2008 | Couture |
| 2008/0058796 A1 * | 3/2008 | O'Brien et al. ................. 606/40 |
| 2008/0071270 A1 * | 3/2008 | Desinger et al. ................ 606/50 |
| 2008/0103494 A1 | 5/2008 | Rioux et al. |
| 2009/0264879 A1 * | 10/2009 | McClurken et al. ............ 606/33 |
| 2010/0100095 A1 | 4/2010 | McClurken et al. |
| 2011/0028965 A1 * | 2/2011 | McClurken .................... 606/33 |
| 2012/0004657 A1 * | 1/2012 | Conley et al. .................. 606/45 |
| 2012/0101496 A1 | 4/2012 | McClurken et al. |
| 2012/0116397 A1 * | 5/2012 | Rencher et al. ................ 606/45 |
| 2012/0191084 A1 | 7/2012 | Davison et al. |

* cited by examiner

METHOD OF PRODUCING AN ELECTROSURGICAL DEVICE

CROSS-REFERENCE TO RELATED APPLICATIONS

This application is a continuation of U.S. application Ser. No. 12/790,309, filed May 28, 2010, now abandoned, and entitled "Fluid-Assisted Electrosurgical Devices, and Methods of Manufacture Thereof", the entire teachings of which are incorporated herein by reference.

FIELD

This invention relates generally to the field of medical systems, devices and methods for use upon a body during surgery. More particularly, the invention relates to electrosurgical systems, devices and methods for use upon tissues of a human body during surgery, particularly open surgery and minimally invasive surgery such as laparoscopic surgery.

BACKGROUND

Dry-tip electrosurgical devices (e.g. monopolar pencil) have been known to cause tissue desiccation, tissue sticking to the electrodes, tissue perforation, char formation and smoke generation. More recently, fluid-assisted electrosurgical devices have been developed which use saline to inhibit such undesirable effects, as well as cool the tissue being treated and electrically couple the device to the tissue. The present invention provides a further improvement to fluid-assisted electrosurgical devices by providing an improved construction which better promotes the manufacture thereof.

SUMMARY

This invention provides a fluid-assisted electrosurgical device to treat tissue in a presence of radio frequency energy and a fluid provided from the device. In one embodiment, the device comprises a handle, a rigid shaft member distal to the handle, and at least one electrode distal to the shaft member. The shaft member comprises a shaft member first body and a shaft member second body joined together along a length of the shaft member. The shaft member further comprises a plurality of longitudinally oriented shaft member passages. The passages may be parallel and positioned along side one another, and have a length defined by the shaft member first body and the shaft member second body. The shaft member first body and the shaft member second body may be made of a plastic material.

In certain embodiments, the plurality of shaft member passages includes an electrical passage containing an electrical conductor, with the electrical conductor electrically coupled to the electrode. The electrical conductor may extend from a proximal end of the shaft member to a distal end of the shaft member where it may be in direct contact with the electrode. The electrical conductor and the electrode may contact one another within a receptacle for the electrode at a distal end of the shaft member. The electrical conductor may be made of sheet metal.

In certain embodiments, the electrical conductor and at least one of the shaft member first body and the shaft member second body may have interconnecting mating features to position the electrical conductor relative to at least one of the shaft member first body and a shaft member second body. The interconnecting mating features may comprise a keyway and a key configured to interconnect with the keyway. In one embodiment, the electrical conductor interconnecting mating feature may comprise the keyway, and the interconnecting mating feature of at least one of the shaft member first body and the shaft member second body may comprise the key configured to interconnect with the keyway. In an alternative embodiment, the keyway may be provided with at least one of the shaft member first body and shaft member second body and the key may be provided with the electrical conductor.

In other embodiments, the plurality of shaft member passages may include a fluid delivery passage, and the fluid delivery passage may be in fluid communication with a fluid outlet configured to provide fluid to the electrode. The fluid outlet may be at least partially defined by the electrode. The shaft member fluid delivery passage may pass through a shaft member connector portion configured to connect the shaft member fluid delivery passage with fluid delivery tubing within the handle. The shaft member connector portion may be defined by at least one of the shaft member first body and the shaft member second body, and may more particularly comprise a barbed connector portion.

In still other embodiments, the device may comprise a first electrode and a second electrode, and the plurality of shaft member passages may include a first electrical passage and a second electrical passage which are isolated from one another. The first electrical passage may contain a first electrical conductor which is electrically coupled to the first electrode, and the second electrical passage may contain a second electrical conductor which is electrically coupled to the second electrode.

In other embodiments, a first fluid outlet may provide fluid to the first electrode and second fluid outlet may provide fluid to the second electrode. The shaft member fluid delivery passage may include a first branch and a second branch. The shaft member fluid delivery passage first branch may be in fluid communication with the first fluid outlet configured to provide fluid to the first electrode, and the shaft member fluid delivery passage second branch may be in fluid communication with the second fluid outlet configured to provide fluid to the second electrode. The first fluid outlet may be at least partially defined by the first electrode, and the second fluid outlet may be at least partially defined by the second electrode.

In other embodiments, the first electrode may include a first electrode fluid delivery passage in fluid communication with the shaft member fluid delivery passage first branch, and the second electrode may include a second electrode fluid delivery passage in fluid communication with the shaft member fluid delivery passage second branch.

In other embodiments, the first electrode fluid delivery passage may pass through a first electrode connector portion configured to connect the first electrode to the shaft member, and the second electrode fluid delivery passage may pass through a second electrode connector portion configured to connect the second electrode to the shaft member. The first electrode connector portion may comprise a barbed connector portion, and the second electrode connector portion may also comprise a barbed connector portion.

In other embodiments, the shaft member first body and the shaft member second body may be welded together. The plurality of longitudinally oriented shaft member passages may be separated from one another along a common weld line or seam.

DETAILED DESCRIPTION

Figure 1:
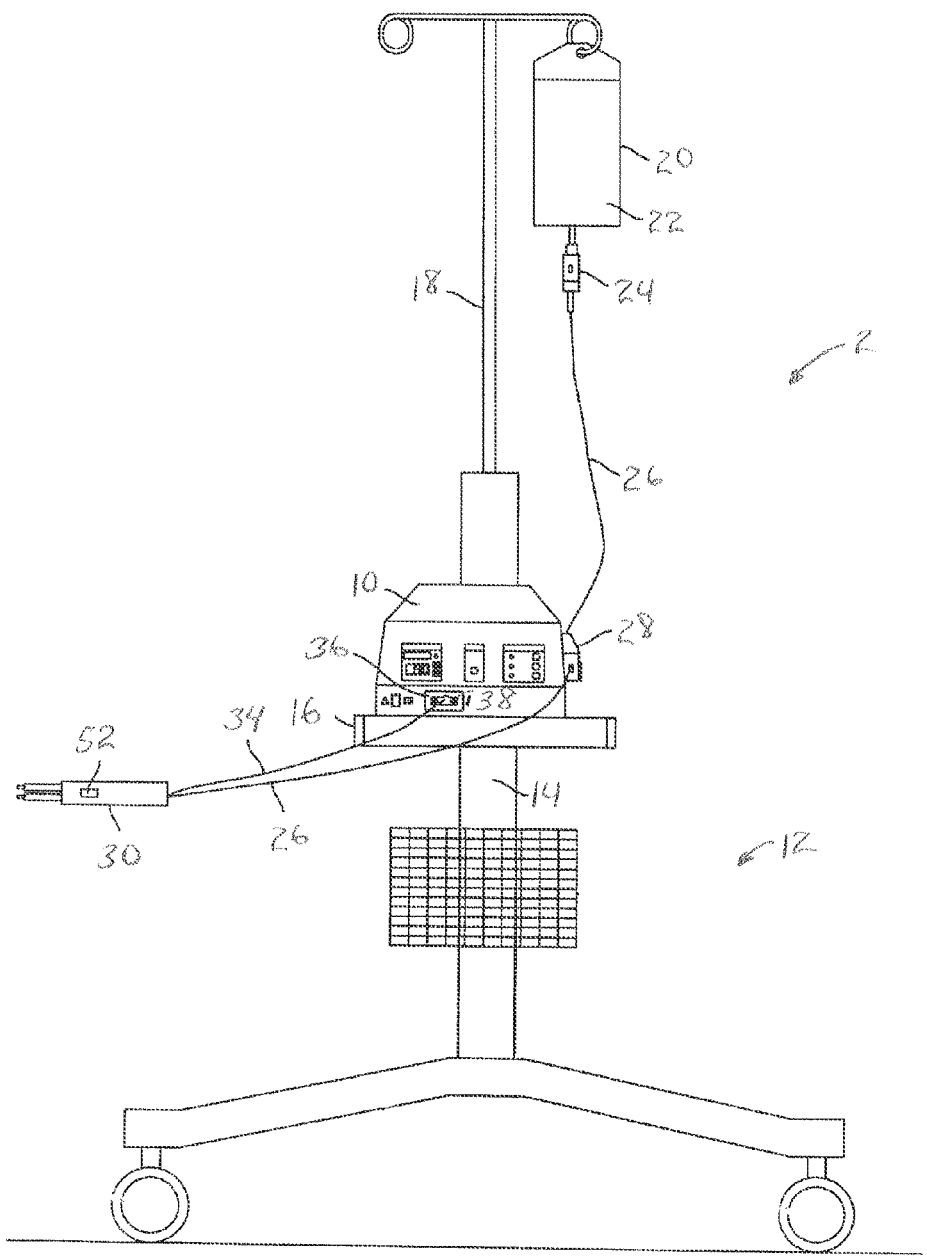
FIG. 1 is a front view of one embodiment of a system of the present invention having an electrosurgical unit in combination with a fluid source and handheld electrosurgical device.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive. From the specification, it should be clear that any use of the terms "distal" and "proximal" are made in reference from the user of the device, and not the patient.

The invention provides systems, devices and methods for treating tissue at a tissue treatment site during an electrosurgical procedure. This is particularly useful for procedures where it is desirable to shrink, coagulate and seal tissue against blood loss, for example, by shrinking lumens of blood vessels (e.g., arteries, veins).

The invention will now be discussed with reference to the figures, with FIG. 1 showing a front view of one embodiment of a system 2 of the present invention having an electrosurgical unit 10 in combination with a fluid source 20 and a handheld electrosurgical device 30. FIG. 1 further shows a movable cart 12 having a support member 14 which carries a platform 16 comprising a pedestal table to provide a flat, stable surface for location of the electrosurgical unit 10. As shown cart 12 further comprises a fluid source carrying pole 18 with a cross support for carrying fluid source 20.

As shown in FIG. 1, fluid source 20 comprises a bag of fluid from which a fluid 22 flows through a drip chamber 24 after the bag is penetrated with a spike located at the end of the drip chamber 24. Thereafter, fluid 22 flows through a fluid passage provided by a lumen of flexible, plastic fluid delivery tubing 26 to handheld electrosurgical device 30.

As shown in FIG. 1, the fluid delivery tubing 26 passes through pump 28. Pump 28 comprises a peristaltic pump and, more specifically, a rotary peristaltic pump. With a rotary peristaltic pump, a portion of the fluid delivery tubing 26 is loaded into the pump 28 by raising and lowering a pump head in a known manner. Fluid 22 is then conveyed within the fluid delivery tubing 26 by waves of contraction placed externally on the tubing 26 which are produced mechanically, typically by rotating pinch rollers which rotate on a drive shaft and intermittently compress the fluid delivery tubing 26 against an anvil support. Alternatively, pump 28 may comprise a linear peristaltic pump. With a linear peristaltic pump, fluid 22 is conveyed within the fluid delivery tubing 26 by waves of contraction placed externally on the tubing 26 which are produced mechanically, typically by a series of compression fingers or pads which sequentially squeeze the tubing 26 against a support. Peristaltic pumps are generally preferred, as the electro-mechanical force mechanism, here rollers driven by electric motor, does not make contact with the fluid 22, thus reducing the likelihood of inadvertent contamination.

In one embodiment, the fluid 22 is liquid saline solution, and even more particularly, normal (physiologic) saline solution. However, although the description herein may make reference to saline as the fluid 22, other electrically conductive fluids may be used in accordance with the invention.

In addition to the use of an electrically conductive fluid, as will become more apparent with further reading of this specification, fluid 22 may also be an electrically non-conductive fluid. The use of a non-conductive fluid may not offer as many advantages as a conductive fluid, however, the use of a non-conductive fluid still provides certain advantages over the use of a dry electrode including, for example, reduced occurrence of tissue sticking to the electrode(s) of device 30 and cooling of the electrode(s) and/or tissue. Therefore, it is also within the scope of the invention to include the use of a non-conductive fluid, such as, for example, deionized water.

As shown in FIG. 1, electrosurgical device 30 is connected to electrosurgical unit 10 via a cable 34 which has a plurality of electrically insulated wire conductors 42 (shown in FIG. 5) and at least one plug 36 at the end thereof. The electrosurgical unit 10 provides radio-frequency (RF) energy via cable 34 to electrosurgical device 30. Plug receptacle 38 of electrosurgical unit 10 receives the plug 36 of device 30 therein to electrically connect device 30 to the electrosurgical unit 10. The fluid delivery tubing 26 may be provided as part of cable 34 and produced with the electrically insulated wire conductors 42 via plastic co-extrusion.

Figure 2:
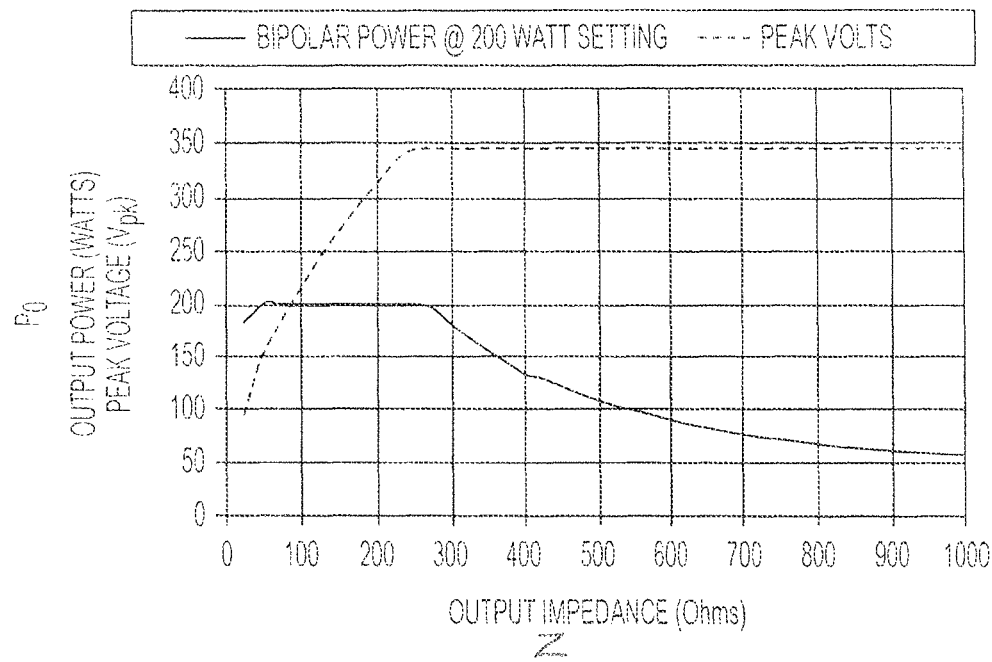
FIG. 2 is a graph of the RF power output versus impedance for the electrosurgical unit of FIG. 1.

An exemplary RF power output curve for electrosurgical unit 10 is shown in FIG. 2. Impedance Z, shown in units of ohms on the X-axis and RF output power $P_O$ is shown in units of watts on the Y-axis. In the illustrated embodiment, the RF power is bipolar and set to 200 watts. As shown in the figure, for an RF power setting $P_S$ of 200 watts, the output power $P_O$ will remain constant with the set RF power $P_S$ as long as the impedance Z stays between the low impedance cut-off of 30 ohms and the high impedance cut-off of 250 ohms. Below an impedance Z of 30 ohms, the output power $P_O$ will decrease as shown by the low impedance ramp. Above an impedance Z of 250 ohms, the output power $P_O$ will also decrease as shown by the high impedance ramp.

Figure 3:
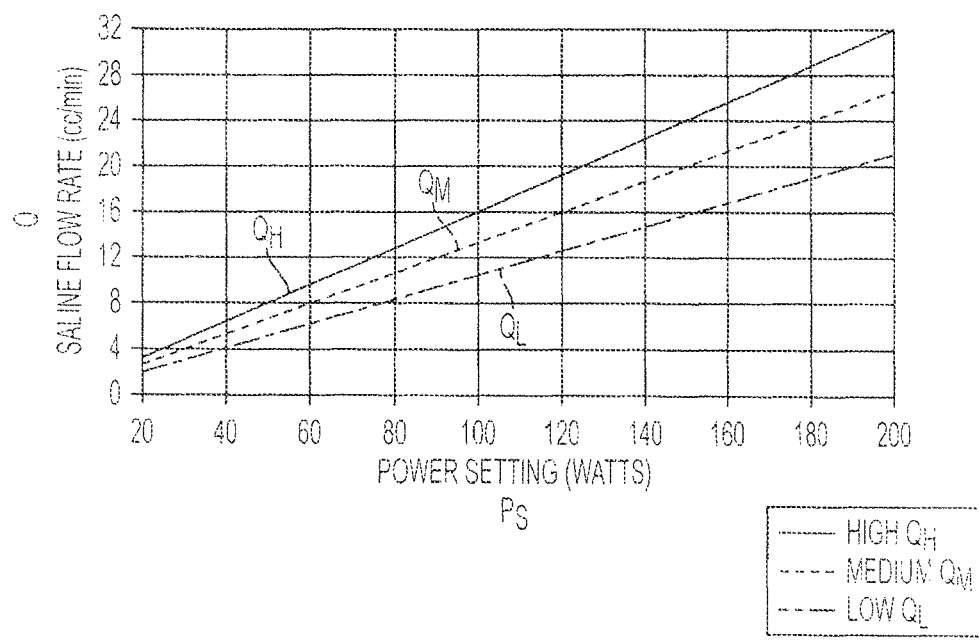
FIG. 3 is graph showing a relationship of fluid flow rate Q in units of cubic centimeters per minute (cc/min) on the Y-axis, and the RF power setting $P_S$ in units of watts on the X-axis.

Electrosurgical unit 10 has also been configured such that the speed of pump 28, and therefore the throughput of fluid 22 expelled by the pump 28, is predetermined based on two input variables, the RF power setting and the fluid flow rate setting. In FIG. 3, there is shown a relationship of fluid flow rate Q in units of cubic centimeters per minute (cc/min) on the Y-axis, and the RF power setting $P_S$ in units of watts on the X-axis. The relationship has been engineered to inhibit undesirable effects such as tissue desiccation, electrode sticking, smoke production and char formation, while at the same time not providing a fluid flow rate Q at a corresponding RF power setting PS which is so great as to provide too much fluid 22 from device 30, which may result in too much electrical dispersion and excess cooling at the electrode/tissue interface.

As shown, electrosurgical unit 10 has been configured to increase the fluid flow rate Q linearly with an increasing RF power setting $P_S$ for each of three fluid flow rate settings of low, medium and high corresponding to $Q_L$, $Q_M$ and $Q_H$, respectively. Conversely, electrosurgical unit 10 has been configured to decrease the fluid flow rate Q linearly with an decrease RF power setting $P_S$ for each of three fluid flow rate settings of low, medium and high corresponding to $Q_L$, $Q_M$ and $Q_H$, respectively.

Electrosurgical unit 10 may be particularly configured for use with an electrosurgical device 30 which is a bipolar device. With a bipolar device, an alternating current (AC) electrical circuit is created between first and second electrical poles/electrodes of the device 30. An exemplary bipolar electrosurgical device of the present invention which may be used in conjunction with electrosurgical unit 10 of the present invention is shown at reference character 30a in FIG. 4. While electrosurgical device 30a of the present invention is described herein with reference to use with electrosurgical unit 10, it should be understood that the description of the combination is for purposes of illustrating the system of the invention. Consequently, it should be understood that while electrosurgical device 30a disclosed herein may be used with electrosurgical unit 10, it may be plausible to use other electrosurgical devices with electrosurgical unit, or it may be plausible to use the electrosurgical device(s) disclosed herein with another electrosurgical unit.

Figure 4:
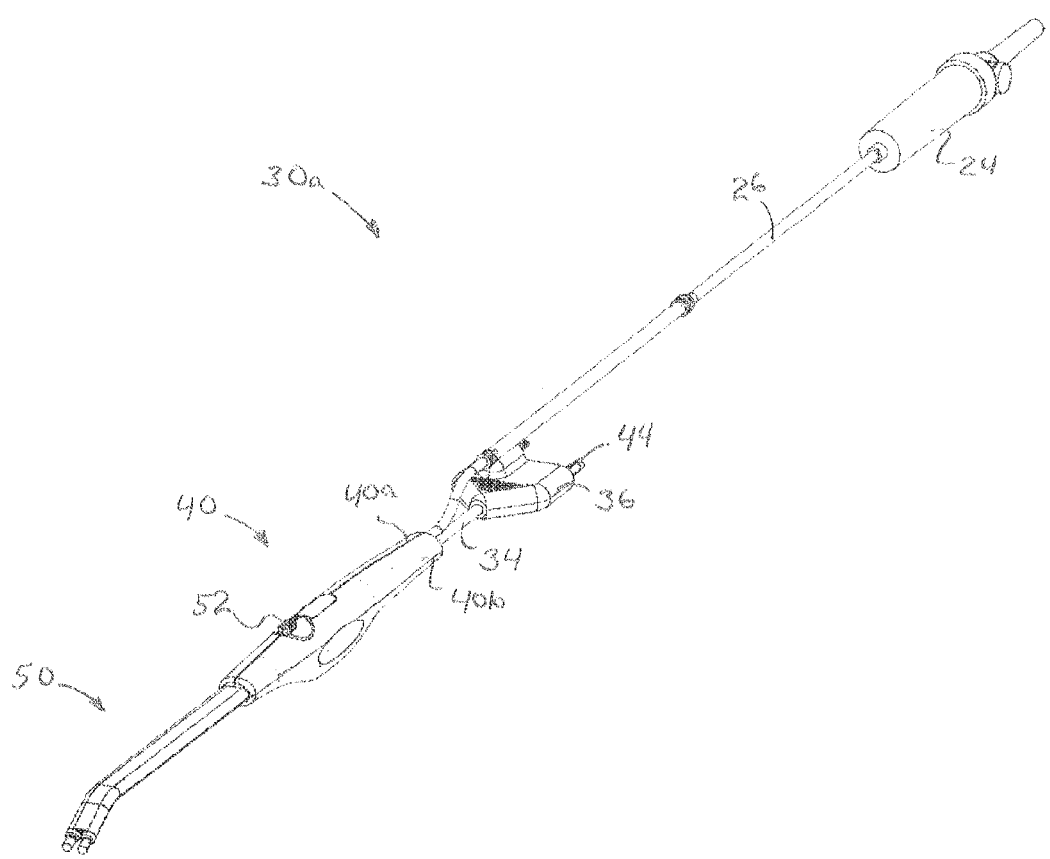
FIG. 4 is a perspective view of an electrosurgical device according to the present invention.

As shown in FIG. 4, exemplary bipolar device 30a comprises a proximal handle 40 comprising mating handle portions 40a, 40b. Handle 40 is preferably made of a sterilizable, rigid, non-conductive material, such as a plastic material (e.g., thermoplastic such as acrylonitrile-butadiene-styrene (ABS), polycarbonate (PC)). Also, handle 40 is preferably configured slender, along with the rest of device 30a, to facilitate a user of device 30a to hold and manipulate device 30a like a pen-type device. Device 30a also includes a cable 34 which is connectable to electrosurgical unit 10 and flexible fluid delivery tubing 26 which is connectable to fluid source 20, particularly via a spike located at the end of drip chamber 24, which respectively provide RF energy and fluid 22 to the electrodes 100, 102.

Figure 5:
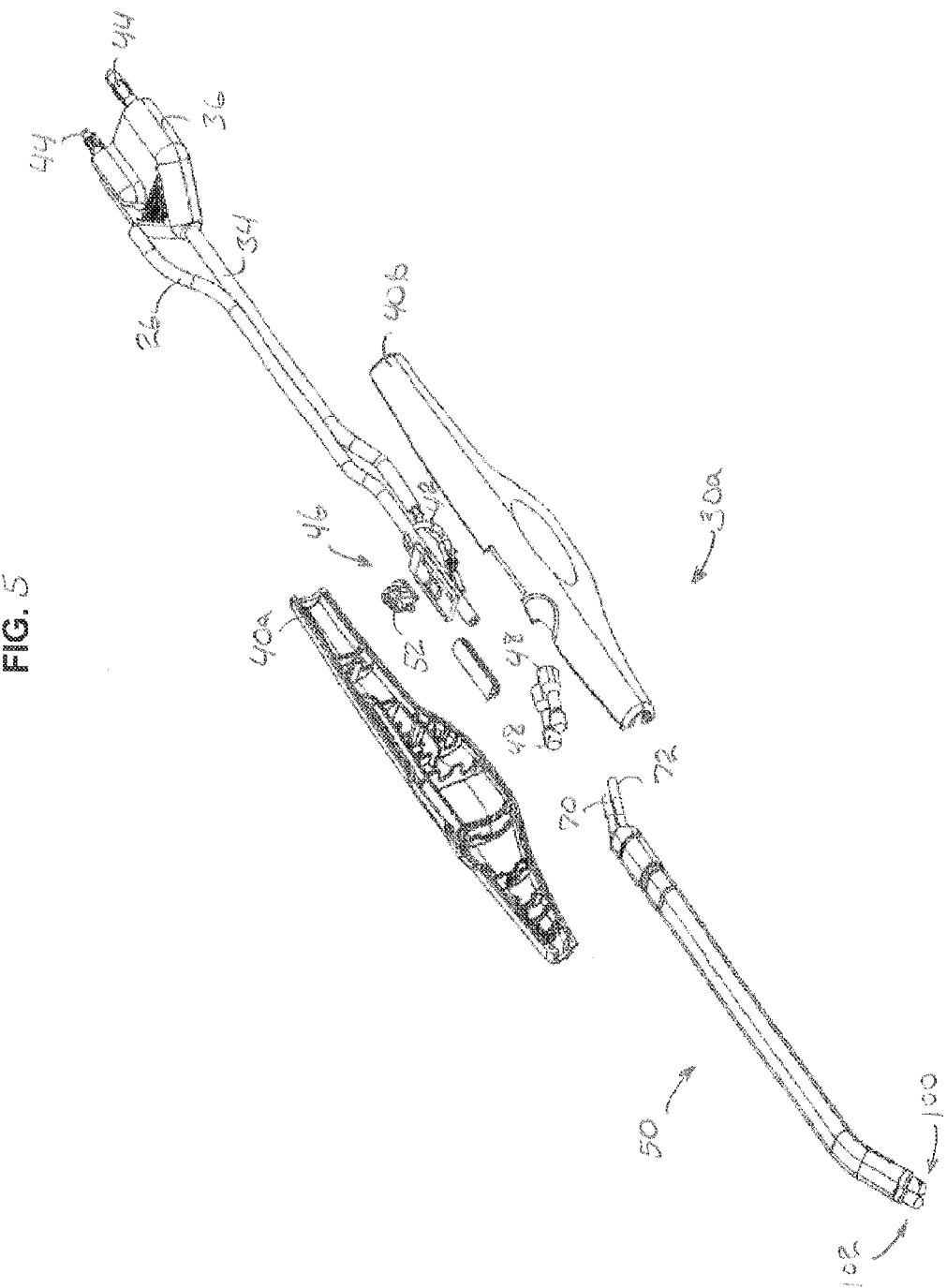
FIG. 5 is an exploded perspective view of the device of FIG. 4.

As shown in FIG. 5, cable 34 of device 30a comprises a plurality of insulated wires 42 connectable to electrosurgical unit 10 via three banana (male) plug connectors 44. The banana plug connectors 44 are each assembled with wire conductors of insulated wires 42 within plug 36 in a known manner. Wire conductors of insulated wires 42 are connected distally to a handswitch assembly 46, and thereafter wire conductors are connected to crimp terminals 48 which connect to a proximal portion of conductors 70, 72 of shaft member 50.

Handswitch assembly 46 comprises a push button 52 which overlies a domed switch. Upon depression of button 52, the domed switch forms a closed circuit which is sensed by electrosurgical unit 10, which then provides RF power to the electrodes 100, 102.

Figure 6:
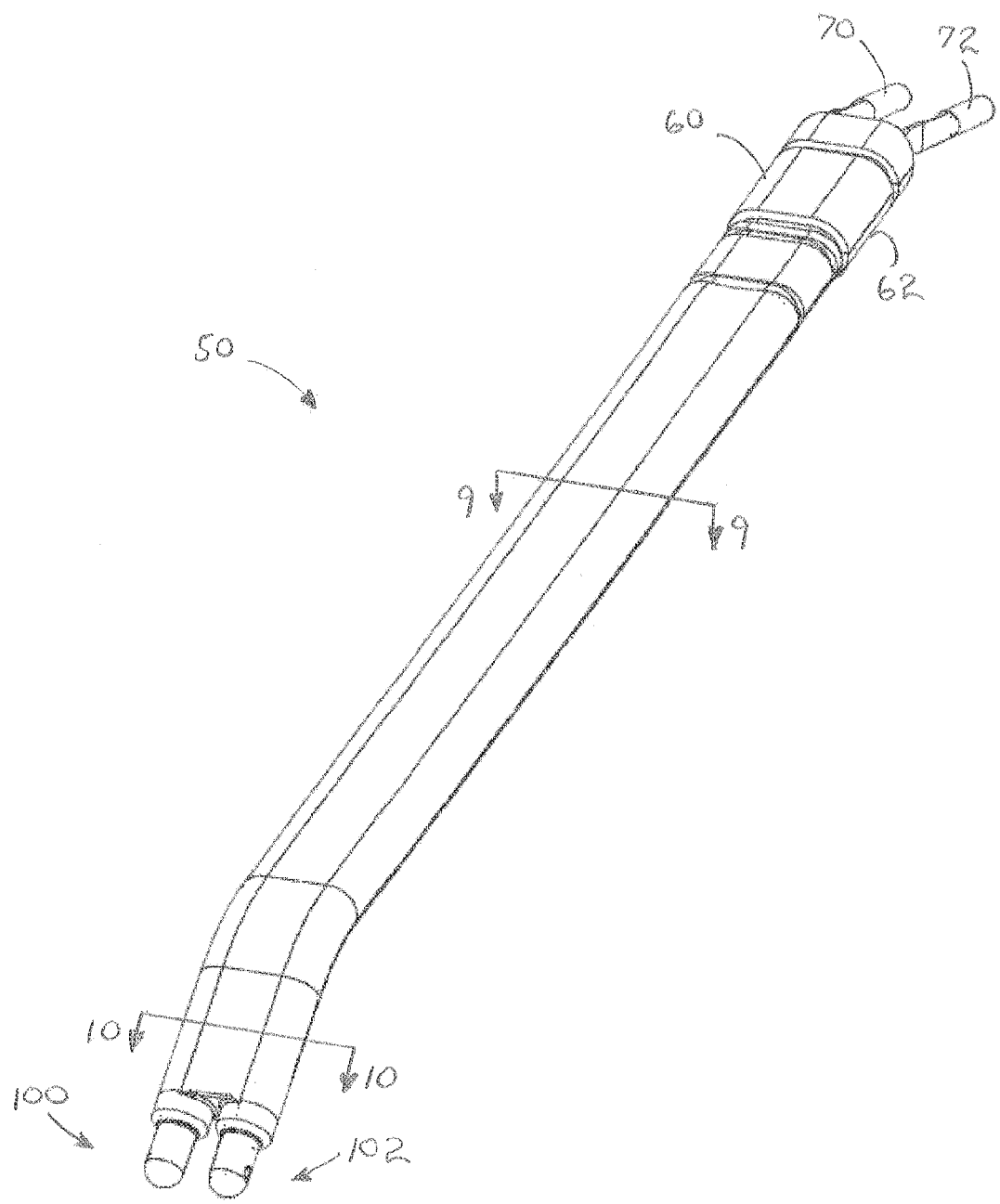
FIG. 6 is a close-up front perspective view of the shaft member of the device of FIG. 4.
Figure 7:
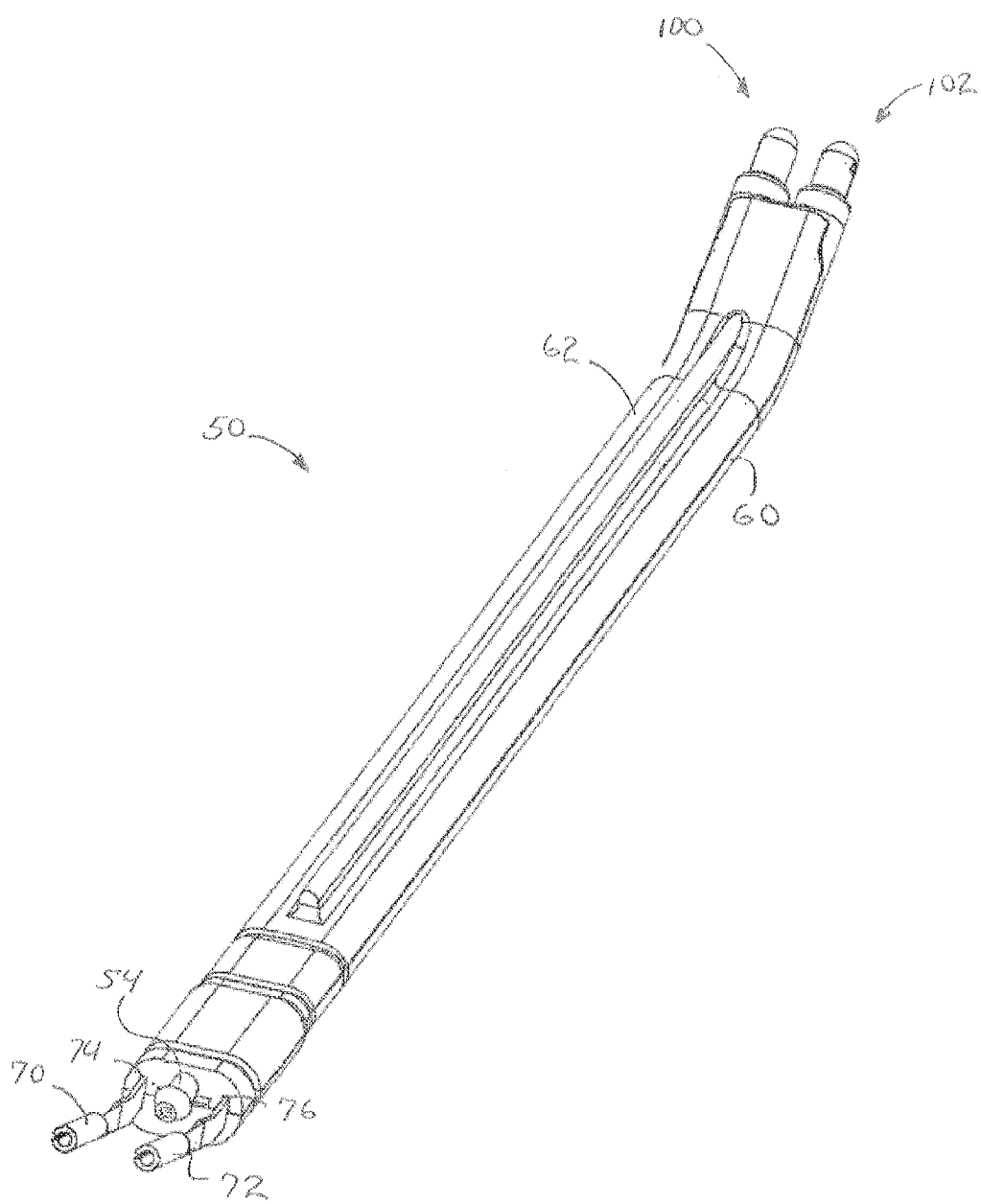
FIG. 7 is a close-up rear perspective view of the shaft member of the device of FIG. 4.

Referring to FIGS. 6 and 7, rigid shaft member 50, located distal to handle 40, comprises a shaft member first body 60 and a shaft member second body 62. Shaft member 50 extends distally from the handle 40 and supports electrodes 100, 102 in rigid relation to the handle 40.

At a proximal end 56 of shaft member 50, fluid delivery tubing 26 of device 30a is connected within handle 40 to a proximal barbed connector portion 54 of shaft member 50, which is defined by at least one of shaft member first body 60 and shaft member second body 62. To connect fluid delivery tubing 26 to barbed connector portion 54, the lumen of fluid delivery tubing 26 preferably interference (friction or press) fit over the outside diameter of barbed connector portion 54 to provide an interference fit and seal therebetween.

Figure 8:
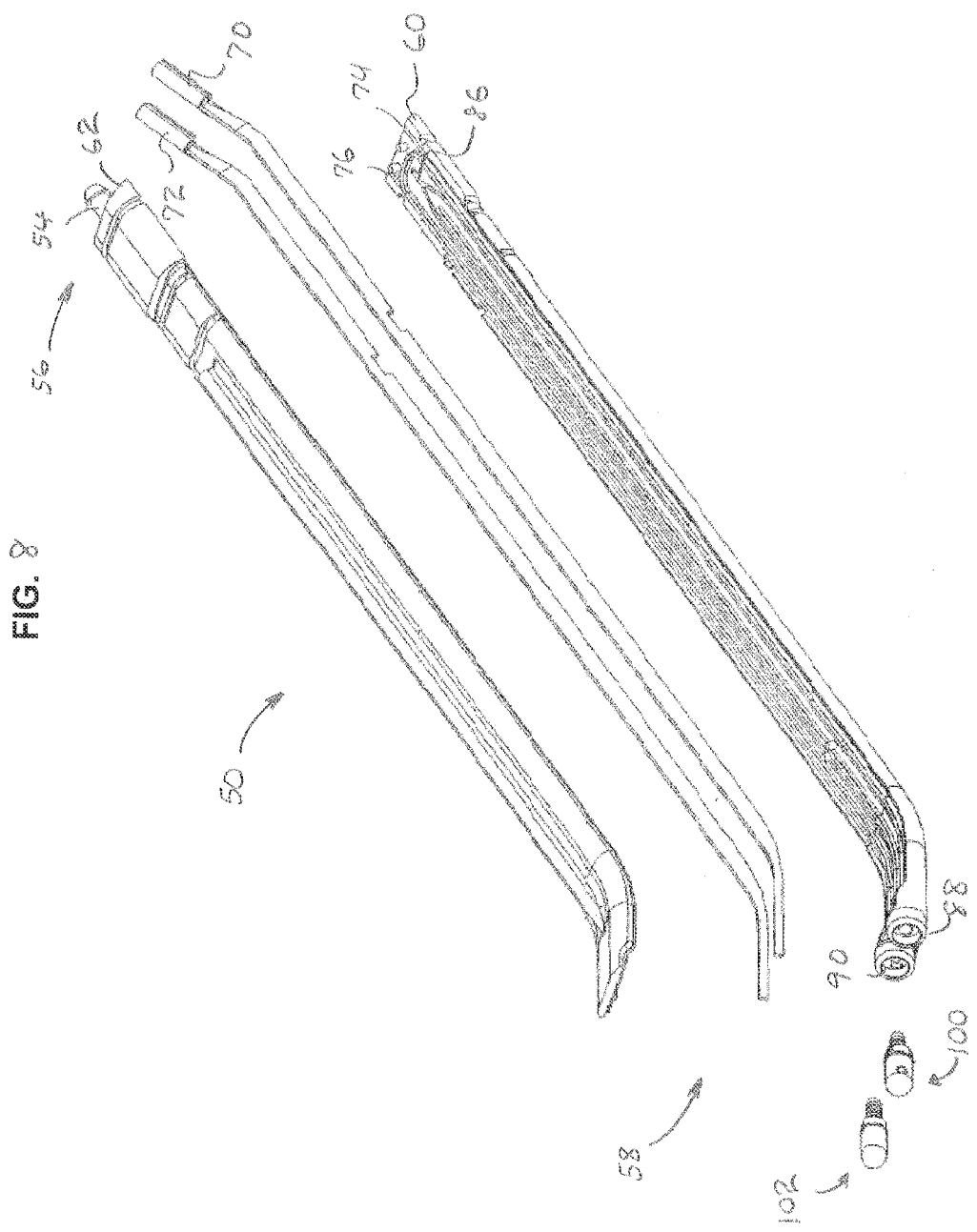
FIG. 8 is an exploded perspective view of the shaft member of FIGS. 6 and 7.
Figure 9:
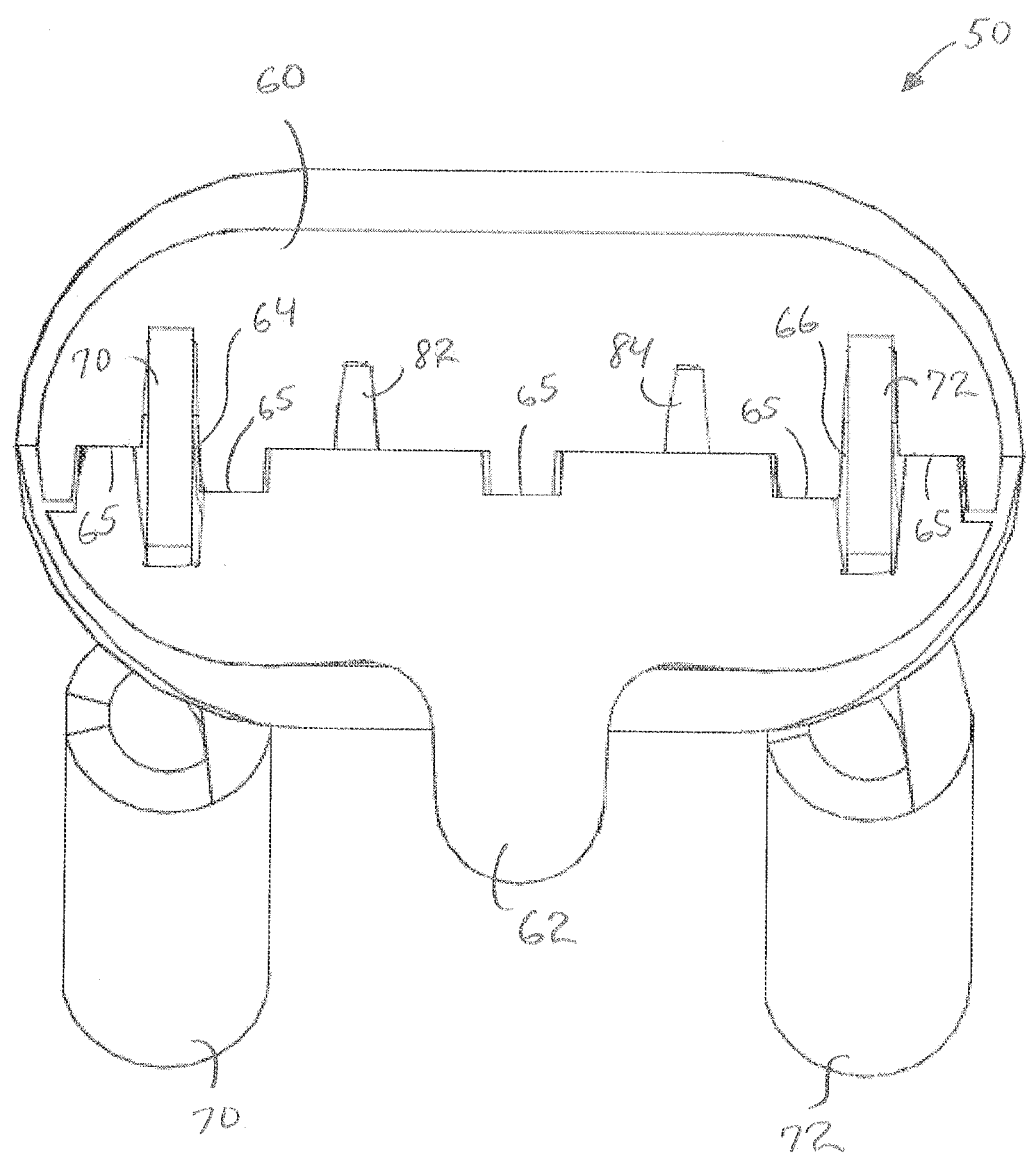
FIG. 9 is a close-up cross-sectional view of the shaft member of FIGS. 6 and 7 taken along line 9-9 of FIG. 6.
Figure 10:
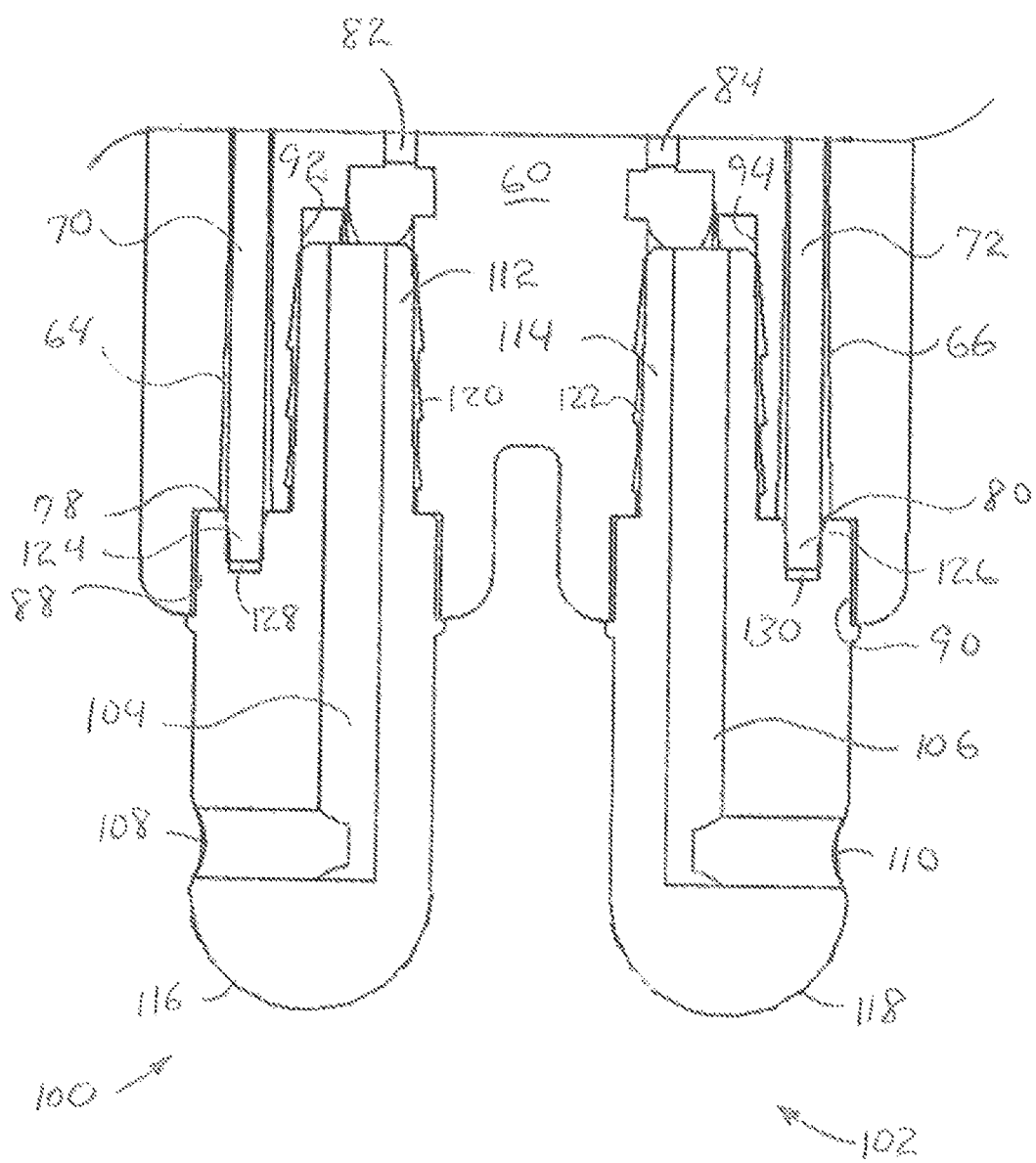
FIG. 10 is a close-up cross-sectional view of the shaft member of FIGS. 6 and 7 taken along line 10-10 of FIG. 6.

As shown in FIGS. 8-10, shaft member first body 60 and shaft member second body 62 comprise two opposing, mating halves of shaft member 50 which may form a clamshell design. Shaft member first body 60 and shaft member second body 62 are joined together along a length of the shaft member 50, from a proximal end 56 to a distal end 58 thereof. Shaft member first body 60 and shaft member second body 62 may particularly be made of a rigid plastic material such as thermoplastic acrylonitrile-butadiene-styrene (ABS) or polycarbonate (PC). As used herein, a rigid plastic may be understood to be a plastic having a modulus of elasticity either in flexure or in tension greater than 700 MPA (100 kpsi) at 23° C. and 50% relative humidity when tested in accordance with ASTM methods D-747, D-790, D-638, or D-882. However, this definition is not necessarily exhaustive, but merely inclusive. Shaft member first body 60 and shaft member second body 62 may be joined by thermoplastic welding, and more particularly ultrasonic welding. In this manner, a hermetic seal may be provided between shaft member first body 60 and shaft member second body 62.

Shaft member 50 includes a plurality of longitudinally oriented, tubular (enclosed), shaft member passages 64, 66, 82 and 84, with each having a length defined by the shaft member first body 60 and the shaft member second body 62. The passages 64, 66, 82 and 84 may be parallel and positioned to a side of one another. As shown, adjacent shaft member passages may be separated from one another by a common weld line or seam 65 which may hermetically seal the passages 64 and 66 from 82 and 84.

Outer (lateral) passages 64, 66 of shaft member 50 more particularly comprise electrical passages which are parallel and isolated from one another, and which contain planar electrical conductors 70, 72. Electrical conductors 70, 72 extend along the complete length of passages 64, 66, and extend from entrance apertures 74, 76, respectively, of passages 64, 66 at a proximal end 56 of shaft member 50, as well as extend from exit apertures 78, 80 of passages 64, 66 at a distal end 58 of shaft member 50. In a particular embodiment, electrical conductors 70, 72 are made of metal, and may more particularly be made of sheet metal. In this manner, conductors are rigid and may contribute to the overall stiffness of shaft member 50.

Also at a proximal end 56 of shaft member 50, electrical conductors 70, 72 are electrically coupled to wire conductors 42 within handle 40 whereby they may receive RF energy conducted through wire conductors 42 from electrosurgical unit 10. At the distal end 58 of shaft member 50, electrical conductors are electrically coupled (via direct physical contact) to electrodes 100, 102, whereby they may conduct the RF energy from electrosurgical unit 10 to electrodes 100, 102. As shown, electrodes 100, 102 are seated in distal end electrode receptacles 88, 90 and electrical conductors 70, 72 extend through apertures 78, 80 within the receptacles 88, 90 at the base thereof for the electrical conductors 70, 72 to make contact with electrodes 100, 102.

Figure 11:
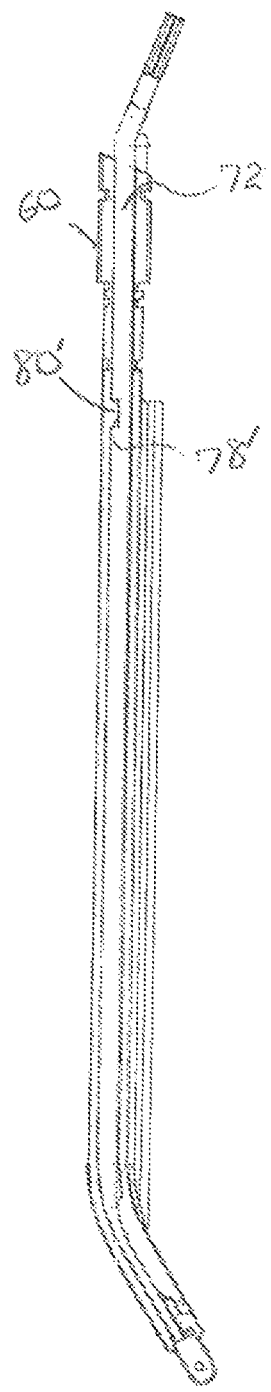
FIG. 11 is a cross-sectional view of the shaft member of FIGS. 6 and 7 taken along a length of conductor 70.

By design, electrical conductors 70, 72 are orientation sensitive and configured to inhibit improper installation within shaft member 50. Furthermore, electrical conductors 70, 72 and at least one of the shaft member first body 60 and the shaft member second body 62 have interconnecting mating features to position each electrical conductor 70, 72 relative to at least one of the shaft member first body 60 and the shaft member second body 62. As shown in FIG. 11, the interconnecting mating feature of each electrical conductor 70, 72 comprises a keyway 78' and the interconnecting mating feature of at least one of the shaft member first body 60 and shaft member second body 62 comprises a key 80' (shown with shaft member first body 60) configured to interconnect with the keyway. In an alternative embodiment, the keyway may be provided with at least one of the shaft member first body 60 and shaft member second body 62 and the key 80 may be provided with the electrical conductor 70, 72.

Returning to FIGS. 8-10, inner (medial) passages 82, 84 of shaft member 50 more particularly comprise fluid delivery passages. At the proximal end 56 of shaft member 50, passages 82, 84 may branch from a common proximal fluid delivery passage 86 which passes through shaft member barbed connector portion 54 and which is in fluid communication/connected with the lumen of fluid delivery tubing 26.

At the distal end 58 of shaft member 50, passages 82, 84 may be in fluid communication with fluid delivery passages 104, 106 which pass through electrodes 100, 102 and terminate in exit apertures 108, 110. As shown, apertures 108, 110 are at least partially defined by electrodes 100, 102, respectively, and more particularly, are completely defined by electrodes 100, 102, respectively. In the foregoing manner, exit apertures 108, 110 provide fluid outlets or exits configured to provide fluid 22 therefrom directly onto electrodes 100, 102. Furthermore, as shown, exit apertures 108, 110 are proximal to a distal end of electrodes 100, 102, as well as located on lateral portions of electrodes 100, 102.

Thus, during use of device 30a, fluid 22 from fluid source 20 is communicated through a tubular passage provided by lumen of fluid delivery tubing 26, after which it flows through tubular fluid delivery passage 86 and tubular fluid delivery passages 82, 84 of shaft member 50, and then to tubular fluid delivery passages 104, 106 of electrodes 100, 102. After flowing through tubular fluid delivery passages 104, 106 of electrodes 100, 102, fluid 22 may be expelled from fluid outlets 108, 110 onto electrodes 100, 102.

As shown in FIG. 10, a female proximal connector portion 92, 94 of each electrode receptacle 88, 90 may be configured to form an interference (friction or press) fit with a male proximal connector portion 112, 114 of each electrode 100, 102. More particularly, the female connector portion 92, 94 of each electrode receptacle 88, 90 may comprise a cylindrical recess and the male connector portion 112, 114 of each electrode 100, 102 may comprise a barbed connector portion 120, 122 configured to fit within the cylindrical recess. In order to increase the efficiency of the design, the first electrode fluid delivery passage 104 may pass through the first electrode connector portion 112 configured to connect the first electrode 100 to the shaft member 50, and the second electrode fluid delivery passage 106 may pass through the second electrode connector portion 114 configured to connect the second electrode 102 to the shaft member 50.

In the illustrated embodiment, electrodes 100, 102 may be configured to slide across a tissue surface in a presence of the RF energy from electrosurgical unit 10 and fluid 22 from the fluid source 20. As shown, electrodes 100, 102 may be laterally and spatially separated (by empty space), and configured as mirror images in size and shape with a blunt distal end surface 116, 118 devoid of edges (to provide a uniform current density and treat tissue without necessarily cutting). More particularly, each distal end surface 116, 118 of electrodes 100, 102 may comprise a spherical surface, and more particularly comprise a hemispherical surface with an arc of 180 degrees. The spherical surface may be defined by a uniform radius along the arc, which may be in the range between and including 1.25 mm to about 2.5 mm. Electrodes 100, 102 may particularly comprise an electrically conductive metal, such as stainless steel. Other suitable materials may include titanium, gold, silver and platinum.

During manufacture of the device 30a, electrical conductors 70, 72 are first installed and positioned with shaft member first body 60. Thereafter, shaft member first body 60 and shaft member second body 62 may be joined by ultrasonic welding. Thereafter, electrodes 100, 102 may be joined to shaft member 50 by inserting male connector portions 112, 114 of electrodes 100, 102 into female connector portions 92, 94 of electrode receptacles 88, 90 of shaft member 50. Prior to inserting male connector portions 112, 114 of electrodes 100, 102 into female connector portions 92, 94, electrodes 100, 102 may be heated. In this manner, electrodes 100, 102 may heat and soften the female connector portions 92, 94 of electrode receptacles 88, 90 during insertion thereof. In this manner, which may be referred to as heat-staking, the insertion force may be reduced, and the plastic material defining female connector portions 92, 94 may flow to better join/grasp with the barbs and adhesively bond, as well as mechanically bond, to electrodes 100, 102. In this manner a hermetic seal may be provided between electrodes 100, 102 and electrode receptacles 88, 90. Alternatively, electrodes 100, 102 may be ultrasonically welded to electrode receptacles 88, 90 of shaft member 50.

At the same time electrodes 100, 102 are joined to shaft member 50 by inserting male connector portions 112, 114 of electrodes 100, 102 into female connector portions 92, 94 of electrode receptacles 88, 90 of shaft member 50, a distal portion 124, 126 of electrical conductors 70, 72 may be inserted into receptacles 128, 130 of electrodes 100, 102 to establish physical contact therewith for electrical communication.

Figure 12:
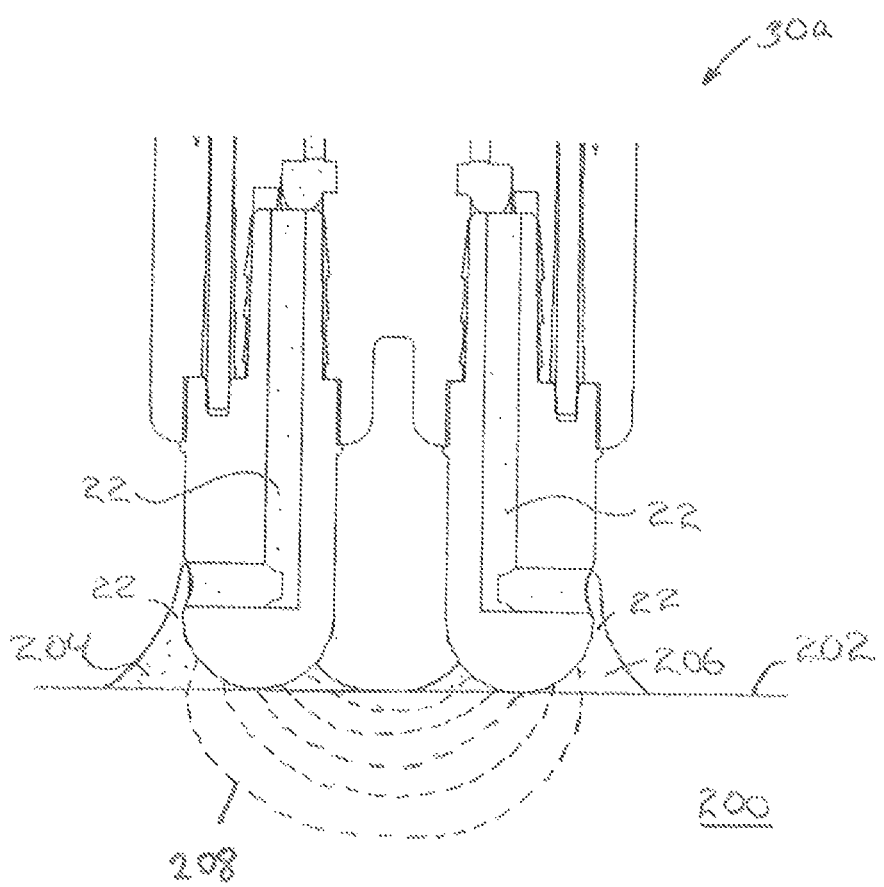
FIG. 12 is a close-up cross-sectional view of a tip portion of the device of FIG. 4 with an exemplary fluid coupling to a tissue surface of tissue.

As shown in FIG. 12, one way in which device 30a may be used is with the longitudinal axis of electrodes 100, 102 vertically orientated, and the spherical surfaces 116, 118 of electrodes 100, 102 laterally spaced adjacent tissue surface 202 of tissue 200. Electrodes 100, 102 are connected to electrosurgical unit 10 to provide RF power and form an alternating current electrical field in tissue 200 located between electrodes 100 and 102. In the presence of alternating current, the electrodes 100, 102 alternate polarity between positive and negative charges with current flow from the positive to negative charge. Without being bound to a particular theory, heating of the tissue 200 is performed by electrical resistance heating.

Fluid 22, in addition to providing an electrical coupling between the device 30a and tissue 200, lubricates surface 202 of tissue 200 and facilitates the movement of electrodes 100, 102 across surface 202 of tissue 200. During movement of electrodes 100, 102, electrodes 100, 102 typically slide across the surface 202 of tissue 200. Typically the user of device 30a slides electrodes 100, 102 across surface 202 of tissue 200 back and forth with a painting motion while using fluid 22 as, among other things, a lubricating coating. Preferably the thickness of the fluid 22 between the distal end surface of electrodes 100, 102 and surface 202 of tissue 200 at the outer edge of couplings 204, 206 is in the range between and including about 0.05 mm to 1.5 mm. Also, in certain embodiments, the distal end tip of electrodes 100, 102 may contact surface 202 of tissue 200 without any fluid 22 in between.

As shown in FIG. 12, fluid couplings 204, 206 comprise discrete, localized webs and more specifically comprise triangular shaped webs providing fluid 22 between surface 202 of tissue 200 and electrodes 100, 102. When the user of electrosurgical device 30a places electrodes 100, 102 at a tissue treatment site and moves electrodes 100, 102 across the surface 202 of the tissue 200, fluid 22 is expelled from fluid outlet openings 108, 110 around and on surfaces 116, 118 of electrodes 100, 102 and onto the surface 202 of the tissue 200 via couplings 204, 206. At the same time, RF electrical energy, shown by electrical field lines 208, is provided to tissue 200 at tissue surface 202 and below tissue surface 202 into tissue 200 through fluid couplings 204, 206.

Device 30a disclosed herein may be particularly useful as non-coaptive tissue sealer in providing hemostasis during surgery. In other words, grasping of the tissue is not necessary to shrink, coagulate and seal tissue against blood loss, for example, by shrinking collagen and associated lumens of blood vessels (e.g., arteries, veins) to provided the desired hemostasis of the tissue. Furthermore, the control system of the electrosurgical unit 10 is not necessarily dependent on tissue feedback such as temperature or impedance to operate. Thus, the control system of electrosurgical unit 10 may be open loop with respect to the tissue which simplifies use.

Device 30a disclosed herein may be particularly useful to surgeons to achieve hemostasis after dissecting through soft tissue, as part of hip or knee arthroplasty. The tissue treating portions can be painted over the raw, oozing surface 202 of tissue 200 to seal the tissue 200 against bleeding, or focused on individual larger bleeding vessels to stop vessel bleeding. As part of the same or different procedure, device 30a is also useful to stop bleeding from the surface of cut bone, or osseous, tissue as part of any orthopaedic procedure that requires bone to be cut. Device 30a may be particularly useful for use during orthopedic knee, hip, shoulder and spine procedures. Additional discussion concerning such procedures may be found in U.S. Publication No. 2006/0149225, published Jul. 6, 2006, and U.S. Publication No. 2005/0090816, published Apr. 28, 2005, which are assigned to the assignee of the present invention and are hereby incorporated by reference in there entirety to the extent they are consistent.

As established above, device 30a of the present invention inhibit such undesirable effects of tissue desiccation, electrode sticking, char formation and smoke generation, and thus do not suffer from the same drawbacks as prior art dry tip electrosurgical devices. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

In an alternative embodiment, device 30a may only have a single electrode 100 and comprise a monopolar device.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

What is claimed is:

1. A method of producing an electrosurgical device, comprising:
    forming a first elongate clamshell and a second elongate clamshell from an electrically insulating material, wherein the first elongate clamshell includes a first face having a plurality of spaced-apart grooves and the second elongate clamshell includes a second face having a second groove opposing one of the plurality of spaced-apart grooves in the first face;
    disposing an electrical conductor into one of the plurality of spaced-apart grooves and the second groove;
    aligning the first face against the second face to interlock the first face with the second face and to form an electrical passage including the electrical conductor and a spaced-apart fluid passage from another groove of the plurality of spaced-apart grooves in the first elongate clamshell;
    welding the first elongate clamshell and the second elongate clamshell together to integrally form a shaft member such that the electrical passage and the fluid passage are each fluid-tight along a major longitudinal portion of the shaft member; and
    attaching an electrode at a distal end of the shaft member to be in electrical communication with the electrical conductor and to form the electrosurgical device.

2. The method of claim 1 including forming a plurality of grooves in the second face.

3. The method of claim 1 wherein the first face and the second face are each substantially planar.

4. The method of claim 1 wherein the electrode is in direct physical contact with the electrical conductor.

5. The method of claim 1 wherein attaching the electrode at the distal end includes attaching the electrode having a fluid passageway through the electrode such that the fluid passageway is in fluid communication with the fluid passage.

6. The method of claim 5 wherein aligning the first face and the second face includes forming a recess in at least one distal end of the first elongate clamshell and the second elongate clamshell such that the fluid passage is in fluid communication with the distal end of the shaft through the recess.

7. The method of claim 6 wherein attaching the electrode at the distal end includes fitting the electrode into the recess.

8. The method of claim 1 wherein one of the first elongate clamshell and the second elongate clamshell includes a first mating feature on one of the first face and the second face, and the other of the first elongate clamshell and the second elongate clamshell includes a second mating feature on the face of the other of the first elongate clamshell and the second elongate clamshell, and wherein aligning the first face and the second face includes interconnecting the mating features.

9. The method of claim 8 wherein the first mating feature include a key and the second mating feature includes a keyway configured to receive the key.

10. The method of claim 1 wherein welding the first elongate clamshell and the second elongate clamshell together includes forming a seam between the passages to hermetically seal the first elongate clamshell and the second elongate clamshell together and to hermetically seal off the passages from each other.

11. The method of claim 1 wherein the electrically insulating material is a thermoplastic.

12. The method of claim 11 wherein attaching the electrode includes heat staking the electrode into the shaft.

13. A method of producing an electrosurgical device, comprising:

forming a first elongate clamshell, wherein the first elongate clamshell includes a first face having a first plurality of spaced-apart grooves;

forming a second elongate clamshell, wherein the second elongate clamshell includes a second face having a second plurality of spaced-apart grooves, wherein at least two of the second plurality of spaced-apart grooves in the second face oppose and correspond with at least two of the first plurality of spaced-apart grooves in the first face;

disposing a first electrical conductor into one of the at least two of the first plurality of spaced apart-grooves;

disposing a second electrical conductor into one of the at least two of the second plurality of spaced apart-grooves;

aligning the first face against the second face to interlock the first face with the second face, wherein the aligning forms a first spaced-apart electrical passage and a second spaced-apart electrical passage each including one of the first electrical conductor and the second electrical conductor, wherein the first electrical passage is formed from aligning one of the at least two of the first plurality of spaced apart-grooves, and wherein the second electrical passage is formed from aligning one of the at least two of the second plurality of spaced apart-grooves, and wherein the aligning forms an elongate fluid passage from one of the at least two of the first plurality of spaced apart-grooves other than the corresponding one of the at least two of the first and second plurality of spaced apart-grooves;

welding the first and second elongate clamshells together to integrally form a shaft member such that the first and second spaced-apart electrical passages and the fluid passage are each fluid-tight along a major longitudinal portion of the shaft member; and attaching a first electrode and a second electrode at a distal end of the shaft member, wherein the first electrode is in electrical communication with the first electrical conductor and the second electrode is in electrical communication with the second electrical conductor to form the electrosurgical device.

14. The method of claim 13 wherein forming the first elongate clamshell includes forming two elongate grooves and wherein forming the second elongate clamshell includes forming at least three grooves.

15. The method of claim 13 wherein the proximal end of the shaft member includes two exit openings in communication with the fluid passage.

16. The method of claim 15 wherein the shaft member includes a proximal end and the proximal end includes one delivery opening in fluid communication with the two exit openings through the fluid passage.

17. The method of claim 15 wherein attaching the first and second electrodes includes fitting the first electrode into one of the two exit openings and fitting the second electrode into the other of the two exit openings.

18. The method of claim 17 wherein fitting the first and second electrodes includes ultrasonically welding the first and second electrodes into the shaft member.

19. The method of claim 13 wherein the first elongate clamshell and the second elongate clamshell are formed from a thermoplastic.

20. The method of claim 19 wherein the welding includes ultrasonically welding the thermoplastic first elongate clamshell and the second elongate clamshell together.

21. A method of producing an electrosurgical device, comprising:

forming a first elongate clamshell having first face including a substantially planar portion;

forming a second elongate clamshell having a second face including a substantially planar portion and a plurality of spaced-apart grooves in the substantially planar portion;

disposing an electrical conductor into one of the plurality of spaced apart grooves;

aligning the first face against the second face to interlock the first face with the second face and form an electrical passage including the electrical conductor from the one of the plurality of spaced-apart grooves and a spaced-apart fluid passage from another one of the plurality of spaced-apart grooves;

welding the first elongate clamshell and the second elongate clamshell together to form a shaft member such that the electrical passage and the fluid passage are each fluid-tight along a major portion of the shaft member; and attaching an electrode at a distal end of the shaft to be in electrical communication with the electrical conductor to form the electrosurgical device.

* * * * *